(12) United States Patent
Estes

(10) Patent No.: US 10,603,433 B2
(45) Date of Patent: Mar. 31, 2020

(54) OPERATING AN INFUSION PUMP SYSTEM

(71) Applicant: Bigfoot Biomedical, Inc., Milipitas, CA (US)

(72) Inventor: Mark C. Estes, Malibu, CA (US)

(73) Assignee: Bigfoot Biomedical, Inc., Milpitas, CA (US)

(*) Notice: Subject to any disclaimer, the term of this patent is extended or adjusted under 35 U.S.C. 154(b) by 184 days.

(21) Appl. No.: 15/848,622

(22) Filed: Dec. 20, 2017

(65) Prior Publication Data

US 2018/0133397 A1  May 17, 2018

Related U.S. Application Data

(63) Continuation of application No. 14/699,341, filed on Apr. 29, 2015, now Pat. No. 9,878,097.

(51) Int. Cl.
| | |
|---|---|
| *A61M 5/172* | (2006.01) |
| *A61M 5/142* | (2006.01) |
| *G16H 20/17* | (2018.01) |
| *A61M 5/14* | (2006.01) |

(52) U.S. Cl.
CPC ...... *A61M 5/1723* (2013.01); *A61M 5/14244* (2013.01); *G16H 20/17* (2018.01); *A61M 2005/1405* (2013.01); *A61M 2005/14208* (2013.01); *A61M 2005/14296* (2013.01); *A61M 2205/52* (2013.01)

(58) Field of Classification Search
CPC .......... A61M 5/1723; A61M 2230/201; A61M 2005/14208; A61M 2005/14268; G06F 19/3468
See application file for complete search history.

(56) References Cited

U.S. PATENT DOCUMENTS

| | | |
|---|---|---|
| 5,984,894 A | 11/1999 | Poulsen |
| 6,126,595 A | 10/2000 | Amano |
| 6,233,471 B1 | 5/2001 | Berner et al. |
| 6,461,331 B1 | 10/2002 | Van Antwerp |
| 6,474,219 B2 | 11/2002 | Klitmose et al. |
| 6,485,461 B1 | 11/2002 | Mason et al. |
| 6,508,788 B2 | 1/2003 | Preuthun |
| 6,524,280 B2 | 2/2003 | Hansen et al. |
| 6,533,183 B2 | 3/2003 | Aasmul et al. |
| 6,537,251 B2 | 3/2003 | Klitmose |
| 6,540,672 B1 | 4/2003 | Simonsen et al. |

(Continued)

FOREIGN PATENT DOCUMENTS

| | | |
|---|---|---|
| CA | 2543545 | 5/2005 |
| DE | 196 27 619 A | 1/1998 |

(Continued)

OTHER PUBLICATIONS

"Using the Deltec Cozmo Insulin Pump Correction Bolus Feature" believed to be publicly available before May 5, 2008, pp. 36-41.

(Continued)

*Primary Examiner* — Emily L Schmidt
(74) *Attorney, Agent, or Firm* — Fish & Richardson P.C.

(57) ABSTRACT

Some embodiments an infusion pump system can be configured to control dispensation of medicine according to a closed-loop delivery mode that is responsive to feedback information provided from a monitoring device, and the infusion pump system permits a user to interrupt the closed-loop delivery mode for purposes of dispensing a user-selected manual bolus dosage.

18 Claims, 9 Drawing Sheets

(56) References Cited

U.S. PATENT DOCUMENTS

| | | |
|---|---|---|
| 6,544,229 B1 | 4/2003 | Danby et al. |
| 6,547,764 B2 | 4/2003 | Larsen et al. |
| 6,551,276 B1 | 4/2003 | Mann et al. |
| 6,554,798 B1 | 4/2003 | Mann et al. |
| 6,554,800 B1 | 4/2003 | Nezhadian et al. |
| 6,558,320 B1 | 5/2003 | Causey, III et al. |
| 6,558,351 B1 | 5/2003 | Steil et al. |
| 6,562,001 B2 | 5/2003 | Lebel et al. |
| 6,562,011 B1 | 5/2003 | Buch-Rasmussen et al. |
| 6,564,105 B2 | 5/2003 | Starkweather et al. |
| 6,569,126 B1 | 5/2003 | Poulsen et al. |
| 6,571,128 B2 | 5/2003 | Lebel et al. |
| 6,572,542 B1 | 6/2003 | Houben |
| 6,577,899 B2 | 6/2003 | Lebel et al. |
| 6,582,404 B1 | 6/2003 | Klitgaard et al. |
| 6,585,644 B2 | 7/2003 | Lebel et al. |
| 6,585,699 B2 | 7/2003 | Ljunggreen et al. |
| 6,605,067 B1 | 8/2003 | Larsen |
| 6,613,019 B2 | 9/2003 | Munk |
| 6,641,533 B2 | 11/2003 | Causey, III et al. |
| 6,648,821 B2 | 11/2003 | Lebel et al. |
| 6,650,951 B1 | 11/2003 | Jones et al. |
| 6,656,158 B2 | 12/2003 | Mahoney et al. |
| 6,656,159 B2 | 12/2003 | Flaherty |
| 6,659,948 B2 | 12/2003 | Lebel et al. |
| 6,659,978 B1 | 12/2003 | Kasuga |
| 6,659,980 B2 | 12/2003 | Moberg et al. |
| 6,663,602 B2 | 12/2003 | Møller |
| 6,668,196 B1 | 12/2003 | Villegas et al. |
| 6,669,669 B2 | 12/2003 | Flaherty et al. |
| 6,687,546 B2 | 2/2004 | Lebel et al. |
| 6,690,192 B1 | 2/2004 | Wing |
| 6,691,043 B2 | 2/2004 | Ribeiro, Jr. |
| 6,692,457 B2 | 2/2004 | Flaherty |
| 6,692,472 B2 | 2/2004 | Hansen et al. |
| 6,694,191 B2 | 2/2004 | Starkweather et al. |
| 6,699,218 B2 | 3/2004 | Flaherty et al. |
| 6,702,779 B2 | 3/2004 | Connelly et al. |
| 6,715,516 B2 | 4/2004 | Ohms et al. |
| 6,716,198 B2 | 4/2004 | Larsen |
| 6,723,072 B2 | 4/2004 | Flaherty et al. |
| 6,723,077 B2 | 4/2004 | Pickup et al. |
| 6,733,446 B2 | 5/2004 | Lebel et al. |
| 6,736,796 B2 | 5/2004 | Shekalim |
| 6,740,059 B2 | 5/2004 | Flaherty |
| 6,740,072 B2 | 5/2004 | Starkweather et al. |
| 6,740,075 B2 | 5/2004 | Lebel et al. |
| 6,744,350 B2 | 6/2004 | Blomquist |
| 6,749,587 B2 | 6/2004 | Flaherty |
| 6,752,787 B1 | 6/2004 | Causey, III et al. |
| 6,758,810 B2 | 7/2004 | Lebel et al. |
| 6,768,425 B2 | 7/2004 | Flaherty et al. |
| 6,780,156 B2 | 8/2004 | Haueter et al. |
| 6,786,246 B2 | 9/2004 | Ohms et al. |
| 6,786,890 B2 | 9/2004 | Preuthun et al. |
| 6,796,970 B1 | 9/2004 | Klitmose et al. |
| 6,799,149 B2 | 9/2004 | Hartlaub |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,827,702 B2 | 12/2004 | Lebel et al. |
| 6,830,558 B2 | 12/2004 | Flaherty et al. |
| 6,852,104 B2 | 2/2005 | Blomquist |
| 6,854,620 B2 | 2/2005 | Ramey |
| 6,854,653 B2 | 2/2005 | Eilersen |
| 6,855,129 B2 | 2/2005 | Jensen et al. |
| 6,872,200 B2 | 3/2005 | Mann et al. |
| 6,873,268 B2 | 3/2005 | Lebel et al. |
| 6,878,132 B2 | 4/2005 | Kipfer |
| 6,893,415 B2 | 5/2005 | Madsen et al. |
| 6,899,695 B2 | 5/2005 | Herrera |
| 6,899,699 B2 | 5/2005 | Enggaard |
| 6,922,590 B1 | 7/2005 | Whitehurst |
| 6,925,393 B1 | 8/2005 | Kalatz et al. |
| 6,936,006 B2 | 8/2005 | Sabra |
| 6,936,029 B2 | 8/2005 | Mann et al. |
| 6,945,961 B2 | 9/2005 | Miller et al. |
| 6,948,918 B2 | 9/2005 | Hansen |
| 6,950,708 B2 | 9/2005 | Bowman, IV et al. |
| 6,960,192 B1 | 11/2005 | Flaherty et al. |
| 6,979,326 B2 | 12/2005 | Mann et al. |
| 6,997,911 B2 | 2/2006 | Klitmose |
| 6,997,920 B2 | 2/2006 | Mann et al. |
| 7,005,078 B2 | 2/2006 | Van Lintel et al. |
| 7,008,399 B2 | 3/2006 | Larson et al. |
| 7,014,625 B2 | 3/2006 | Bengtsson |
| 7,018,360 B2 | 3/2006 | Flaherty et al. |
| 7,025,743 B2 | 4/2006 | Mann et al. |
| 7,029,455 B2 | 4/2006 | Flaherty |
| 7,054,836 B2 | 5/2006 | Christensen et al. |
| 7,104,972 B2 | 9/2006 | Møller et al. |
| 7,109,878 B2 | 9/2006 | Mann et al. |
| 7,128,727 B2 | 10/2006 | Flaherty et al. |
| 7,133,329 B2 | 11/2006 | Skyggebjerg et al. |
| 7,232,423 B2 | 6/2007 | Mernoe et al. |
| 7,278,983 B2 | 10/2007 | Ireland et al. |
| 7,291,107 B2 | 11/2007 | Hellwig et al. |
| 8,548,544 B2 | 10/2013 | Kircher et al. |
| 2001/0056262 A1 | 12/2001 | Cabiri |
| 2002/0004651 A1 | 1/2002 | Ljndggreen et al. |
| 2002/0007154 A1 | 1/2002 | Hansen et al. |
| 2002/0040208 A1 | 4/2002 | Flaherty et al. |
| 2002/0091358 A1 | 7/2002 | Klitmose |
| 2002/0126036 A1 | 9/2002 | Flaherty et al. |
| 2003/0055380 A1 | 3/2003 | Flaherty |
| 2003/0065308 A1 | 4/2003 | Lebel et al. |
| 2003/0088238 A1 | 5/2003 | Poulsen |
| 2003/0104982 A1 | 6/2003 | Wittmann et al. |
| 2003/0199825 A1 | 10/2003 | Flaherty |
| 2003/0216683 A1 | 11/2003 | Shekalim |
| 2004/0010207 A1 | 1/2004 | Flaherty et al. |
| 2004/0019325 A1 | 1/2004 | Shekalim |
| 2004/0064088 A1 | 4/2004 | Gorman et al. |
| 2004/0064096 A1 | 4/2004 | Flaherty et al. |
| 2004/0078028 A1 | 4/2004 | Flaherty et al. |
| 2004/0087894 A1 | 5/2004 | Flaherty |
| 2004/0092865 A1 | 5/2004 | Flaherty et al. |
| 2004/0092878 A1 | 5/2004 | Flaherty |
| 2004/0116866 A1 | 6/2004 | Gorman et al. |
| 2004/0127844 A1 | 7/2004 | Flaherty |
| 2004/0153032 A1 | 8/2004 | Garribotto et al. |
| 2004/0167464 A1 | 8/2004 | Ireland et al. |
| 2004/0171983 A1 | 9/2004 | Sparks et al. |
| 2004/0176720 A1 | 9/2004 | Kipfer |
| 2004/0176727 A1 | 9/2004 | Shekalim |
| 2004/0204673 A1 | 10/2004 | Flaherty |
| 2004/0220551 A1 | 11/2004 | Flaherty et al. |
| 2004/0235446 A1 | 11/2004 | Flaherty et al. |
| 2004/0260233 A1 | 12/2004 | Garibotto et al. |
| 2005/0021005 A1 | 1/2005 | Flaherty et al. |
| 2005/0022274 A1 | 1/2005 | Campbell et al. |
| 2005/0065760 A1 | 3/2005 | Murtfeldt et al. |
| 2005/0090808 A1 | 4/2005 | Malave et al. |
| 2005/0095063 A1 | 5/2005 | Fathallah |
| 2005/0160858 A1 | 7/2005 | Mernoe |
| 2005/0171512 A1 | 8/2005 | Flaherty |
| 2005/0182366 A1 | 8/2005 | Vogt et al. |
| 2005/0192561 A1 | 9/2005 | Mernoe |
| 2005/0203461 A1 | 9/2005 | Flaherty et al. |
| 2005/0215982 A1 | 9/2005 | Estes |
| 2005/0222645 A1 | 10/2005 | Malave et al. |
| 2005/0238507 A1 | 10/2005 | DiIanni et al. |
| 2005/0245878 A1 | 11/2005 | Mernoe et al. |
| 2005/0251097 A1 | 11/2005 | Mernoe |
| 2005/0267402 A1 | 12/2005 | Stewart et al. |
| 2005/0273059 A1 | 12/2005 | Mernoe et al. |
| 2006/0041229 A1 | 2/2006 | Garibotto et al. |
| 2006/0069382 A1 | 3/2006 | Pedersen |
| 2006/0074381 A1 | 4/2006 | Malave et al. |
| 2006/0135913 A1 | 6/2006 | Ethelfeld |
| 2006/0142698 A1 | 6/2006 | Ethelfeld |
| 2006/0173406 A1 | 8/2006 | Hayes et al. |

(56) References Cited

U.S. PATENT DOCUMENTS

| | | |
|---|---|---|
| 2006/0178633 A1 | 8/2006 | Garibotto et al. |
| 2006/0184119 A1 | 8/2006 | Remde et al. |
| 2006/0200073 A1 | 9/2006 | Radmer et al. |
| 2006/0206054 A1 | 9/2006 | Shekalim |
| 2006/0247581 A1 | 11/2006 | Pedersen et al. |
| 2007/0073228 A1 | 3/2007 | Mernoe et al. |
| 2007/0073235 A1 | 3/2007 | Estes et al. |
| 2007/0073236 A1 | 3/2007 | Mernoe et al. |
| 2007/0118405 A1 | 5/2007 | Campbell et al. |
| 2007/0124002 A1 | 5/2007 | Estes et al. |
| 2007/0156092 A1 | 7/2007 | Estes et al. |
| 2007/0167905 A1 | 7/2007 | Estes et al. |
| 2007/0167912 A1 | 7/2007 | Causey et al. |
| 2007/0173761 A1 | 7/2007 | Kanderian, Jr. et al. |
| 2007/0179444 A1 | 8/2007 | Causey et al. |
| 2008/0125700 A1 | 5/2008 | Moberg et al. |
| 2008/0172027 A1 | 7/2008 | Blomquist |
| 2008/0177165 A1 | 7/2008 | Blomquist et al. |
| 2008/0294094 A1 | 11/2008 | Mhatre et al. |
| 2008/0294142 A1 | 11/2008 | Patel et al. |
| 2008/0306434 A1 | 12/2008 | Dobbles et al. |
| 2008/0306444 A1 | 12/2008 | Brister |
| 2010/0174266 A1 | 7/2010 | Estes |
| 2010/0286601 A1 | 11/2010 | Yodfat |
| 2010/0298765 A1 | 11/2010 | Budiman |
| 2012/0016304 A1 | 1/2012 | Patel et al. |
| 2014/0066890 A1 | 3/2014 | Sloan et al. |
| 2014/0180203 A1 | 6/2014 | Budiman et al. |
| 2014/0309615 A1 | 10/2014 | Mazlish |
| 2014/0323959 A1 | 10/2014 | Lebel et al. |

FOREIGN PATENT DOCUMENTS

| | | |
|---|---|---|
| DE | 102 36 669 | 2/2004 |
| DE | 20 2005 012 358 | 10/2005 |
| EP | 0 062 974 | 10/1982 |
| EP | 0 275 213 | 7/1988 |
| EP | 0 496 141 | 7/1992 |
| EP | 0 612 004 | 8/1994 |
| EP | 0 580 723 | 10/1995 |
| EP | 1 045 146 | 12/2000 |
| EP | 1 136 698 | 9/2001 |
| EP | 1 177 802 | 2/2002 |
| EP | 0 721 358 | 5/2002 |
| EP | 1 495 775 | 1/2005 |
| EP | 1 527 792 | 5/2005 |
| EP | 1 754 498 | 2/2007 |
| EP | 1 818 664 | 8/2007 |
| FR | 2 585 252 | 1/1987 |
| GB | 747 701 | 4/1956 |
| GB | 2 218 831 | 11/1989 |
| WO | WO 90/15928 | 12/1990 |
| WO | WO 97/21457 | 6/1997 |
| WO | WO 98/11927 | 3/1998 |
| WO | WO 98/57683 | 12/1998 |
| WO | WO 99/21596 | 5/1999 |
| WO | WO 99/39118 | 8/1999 |
| WO | WO 99/48546 | 9/1999 |
| WO | WO 01/72360 | 10/2001 |
| WO | WO 01/91822 | 12/2001 |
| WO | WO 01/91833 | 12/2001 |
| WO | WO 02/40083 | 5/2002 |
| WO | WO 02/057627 | 7/2002 |
| WO | WO 02/100469 | 12/2002 |
| WO | WO 03/103763 | 12/2003 |
| WO | WO 04/056412 A2 | 7/2004 |
| WO | WO 04/093648 | 11/2004 |
| WO | WO 04/110526 A | 12/2004 |
| WO | WO 05/002652 | 1/2005 |
| WO | WO 05/039673 | 5/2005 |
| WO | WO 05/072794 | 8/2005 |
| WO | WO 05/072795 | 8/2005 |
| WO | WO 06/075016 | 7/2006 |
| WO | WO 06/105792 | 10/2006 |
| WO | WO 06/105793 | 10/2006 |
| WO | WO 06/105794 | 10/2006 |

OTHER PUBLICATIONS

"Which Insulin Pump is Right for Me?", Albany Medical Center, Goodman Diabetes Service, Jan. 2006, 4 pages.

Asante Pearl, Insulin Pump User Manual, 2012, 180 pages.

Collins and Lee, "Microfluidic flow transducer based on the measurement of electrical admittance," *Lab Chip*, 2003, 12 pages.

Debiotech News Release, "Debiotech reveals its new miniaturized Disposable Insulin Nanopump™ for Diabetes therapy," available at http://www.debiotech.com/news/nw_159.html Apr. 24, 2006, 3 pages.

Medtronic News Release, "Medtronic Receives FDA Approval for World's First Insulin Pump with Real-time Continuous Glucose Monitoring," Apr. 13, 2006, 3 pages.

Patent Abstracts of Japan, vol. 1999, No. 04, and JP 11 010036, Apr. 30, 1999 and Jan. 19, 1999, Toray Ind. Inc., 6 pages.

Walsh et al., "Guidelines for Insulin Dosing in Continuous Subcutaneious Insulin Infusion Using New Formulas from a Retrospective Study of Individuals with Optimal Glucose Levels", *J. Diabetes Science and Technology*, Sep. 2010, 4(5):8 pages.

Walsh et al., "Guidelines for Optimal Bolus Calculator Settings in Adults", *J. Diabetes Science and Technology*, Jan. 2011, 5(1):7 pages.

International Search Report and Written Opinion in International Application No. PCT/US2016/029440, dated Sep. 27, 2016, 12 pages.

International Preliminary Report of Patentability in International Application No. PCT/US2016/029440, dated Nov. 9, 2017, 10 pages.

Invitation to Pay Additional Fees and where applicable, protest fee in International Application No. PCT/US2016/029440 dated Jul. 28, 2016, 2 pages.

European Extended Search Report in European Application No. 16787016.1, dated Mar. 21, 2018, 9 pages.

OPERATING AN INFUSION PUMP SYSTEM

CROSS-REFERENCE TO RELATED APPLICATIONS

This application is a continuation application of and claims priority to U.S. application Ser. No. 14/699,341, filed on Apr. 29, 2015.

TECHNICAL FIELD

This document relates to an infusion pump system, such as a portable infusion pump system for dispensing insulin or another medicine.

BACKGROUND

Pump devices are commonly used to deliver one or more fluids to a targeted individual. For example, a medical infusion pump device may be used to deliver a medicine to a patient as part of a medical treatment. The medicine that is delivered by the infusion pump device can depend on the condition of the patient and the desired treatment plan. For example, infusion pump devices have been used to deliver insulin to the vasculature of diabetes patients so as to regulate blood-glucose levels.

Infusion pump devices often seek to deliver medicine in accurately controlled dosages. Over-dosages and under-dosages of medicine can be detrimental to patients. For example, an infusion pump device that delivers an over-dosage or under-dosage of insulin to a diabetes patient can significantly affect the blood-glucose level of the patient.

Some insulin pump devices may control the dispensation of insulin using a closed-loop controller in which the insulin dispensation is automatically adjusted in response to sensor feedback indicative of a user's blood glucose level. For example, these pump devices that operate using a closed-loop controller would subsequently increase the insulin dispensation after detecting a rise in a user's blood glucose level (e.g., after the user has consumed a meal). Some of these closed-loop insulin pump devices purport to act as an "artificial pancreas" in which no user input is prompted when the controller adjusts the insulin dispensation.

SUMMARY

Some embodiments of an infusion pump system described herein can be configured to control the dispensation of medicine (e.g., insulin) according to an interruptible closed-loop delivery mode. During the closed-loop delivery mode, the infusion pump system may autonomously dispense medication to the user based on a sensed physiological state. For example, the infusion pump system may dispense insulin to a user in response to the user's blood glucose level while operating in a closed-loop delivery mode. In some embodiments, the closed-loop delivery mode may be temporarily interrupted to accommodate a user-prompted bolus dosage. For example, the user may elect to manually enter a specific bolus dosage or to initiate the calculation of a suggested bolus dosage by accessing a user interface of the infusion pump system. Optionally, the infusion pump system is configured to perform one or more dosage calculations for purposes of providing the user-prompted bolus dosage. Such a bolus dosage calculation may account for medication dispensed during operations in the closed-loop delivery mode over a predetermined time period immediately prior to the calculation. Thus, in some embodiments, the infusion pump system is configured to calculate the amount of effective insulin-on-board (eIOB), which corresponds to the net amount of remaining active insulin in the user's system from dosages during the predetermined time period.

Particular embodiments described herein include a method of operating a portable insulin infusion pump system. The method may include detecting a trigger event to initiate a user-selected manual bolus dosage while operating an infusion pump system to dispense insulin according to a closed-loop delivery mode. The method may further include temporarily interrupting the closed-loop delivery mode by dispensing from the infusion pump system the user-selected manual bolus dosage. Also, the method may include automatically returning to the closed-loop delivery mode after dispensation of the user-selected manual bolus dosage. A calculated dosage amount of the user-selected manual bolus dosage may be calculated by the infusion pump system based upon at least both user input of a particular value(s) and a calculated amount of insulin previously dispensed during the closed-loop delivery mode over a time period immediately prior to interruption of the closed-loop delivery mode.

In some embodiments, a method of operating a portable insulin infusion pump system may include detecting a trigger event to initiate a user-selected manual bolus dosage while operating an infusion pump system to dispense insulin according to a closed-loop delivery mode. The method may also include determining, at the infusion pump system, that the user-selected manual bolus dosage is permissible based on (at least) an amount of the bolus dosage and a calculated amount of insulin previously dispensed during the closed-loop delivery mode over a time period immediately prior to the trigger event. The method may further include initiating delivery of the permissible bolus dosage.

In certain embodiments, a method of operating a portable insulin infusion pump system may include detecting a trigger event to initiate a user-selected manual bolus dosage while operating an infusion pump system to dispense insulin according to a closed-loop delivery mode in which insulin is dispensed in response to feedback information of a user's blood glucose characteristic. Optionally, the method may further include temporarily interrupting the closed-loop delivery mode by dispensing from the infusion pump system the user-selected manual bolus dosage. Also, the method may include automatically returning to the closed-loop delivery mode after dispensation of the user-selected manual bolus dosage.

According to one or more embodiments, the closed-loop delivery mode causes the infusion pump system to dispense insulin in response to feedback information of a user's blood glucose level, and the trigger event includes actuation of a user interface button indicating a user's request to manually initiate a bolus dispensation that is independent from the feedback information of the user's blood glucose characteristic. According to one or more embodiments, the user-selected manual bolus dosage is dispensed independently of the feedback information of the user's blood glucose characteristic.

According to one or more embodiments, the trigger event includes actuation of a user interface button indicating a user's request to initiate calculation of a suggested bolus dosage by the infusion pump system.

According to one or more embodiments, the infusion pump system includes a controller, which may optionally comprise a user interface display device and control circuitry arranged in a controller housing and being programmed to perform the calculation of the manual bolus dosage. According to one or more embodiments, the infusion pump system may also include a pump device, which may optionally comprise a pump housing that houses a drive system and a space to receive a medicine (e.g., insulin in particular implementations). Also, in some embodiments, the controller housing may be removably mountable to the pump housing so that the controller is electrically connected to components of the pump device (e.g., the drive system, other components, or a combination thereof).

According to one or more embodiments, the amount of insulin dispensed during the closed-loop delivery mode over the time period includes an effective-insulin-on-board amount calculated as follows:

$$\text{Effective Insulin-on-Board} = [\Sigma(\text{Dosage}_n * \text{Duration Factor}(t)n)] - \text{Estimated Basal Rate},$$

where n is any positive whole number, and where Duration Factor$(t)_n$, represents a factor discounting the dosage based on an amount of time (t) since its delivery. According to one or more embodiments, the method further includes outputting an alert from the infusion pump system in response to a calculated stacking value exceeding a predetermined stacking threshold, the calculated stacking value includes the calculated dosage amount of the user-selected manual bolus dosage plus the Effective Insulin-on-board. According to one or more embodiments, the calculated dosage amount of the user-selected manual bolus dosage includes include a calculation of a suggested bolus dosage according to the following function:

$$\text{Suggested Bolus Dosage} = (\text{Food Offsetting Component}) + (\text{Blood Glucose Correction Component}) - (\text{Effective Insulin-on-board Component}).$$

According to one or more embodiments, the Estimated Basal Rate is calculated according to the following function:

$$\text{Estimated Basal Rate} = \text{Total Dose}/(T * \text{Scale Down Factor}),$$

where T is a unit of time.

Particular embodiments described herein include a medical infusion pump system, which may be (optionally) configured as a wearable pump system to dispense insulin or another medicine to a user. The system may include a portable pump housing configured to receive medicine for dispensation to a user. The pump housing may at least partially contain a pump drive system to dispense the medicine through a flow path to the user. The system may also include a controller that controls the pump drive system to dispense the medicine from the portable pump housing according to a closed-loop delivery mode in which, for example, the controller autonomously provides insulin dosages to the user in response to feedback information of a user's blood glucose level. The controller may be configured to, in response to receiving input indicative of a user-prompted bolus dosage, temporarily interrupt the closed-loop delivery mode by dispensing from the infusion pump system the user-prompted bolus dosage. The calculated dosage amount of the user-prompted bolus dosage is calculated by the infusion pump system based upon both user input of a particular value(s) and a calculated amount of insulin previously dispensed during the closed-loop delivery mode over a predetermined time period prior to the user-prompted bolus dosage.

According to one or more embodiments, the input indicative of the user-prompted bolus dosage includes actuation of a user interface button indicating a user request to manually enter a bolus dosage amount.

According to one or more embodiments, the input indicative of the user-prompted bolus dosage includes actuation of a user interface button indicating a user request to initiate a calculation, by the infusion pump system, of a suggested bolus dosage.

According to one or more embodiments, the controller includes a user interface including a display device and a plurality of buttons. According to one or more embodiments, the controller includes a controller housing that removably attaches to the pump housing. According to one or more embodiments, the controller is electrically connected to the pump drive system when the controller housing is removably attached to the pump housing. According to one or more embodiments, the controller is a reusable device and the pump housing and pump drive system are disposable and nonreusable (e.g., one or more structural components of the pump device that hinder reuse of the pump device after exhaustion of the medicine supply in the pump device).

According to one or more embodiments, the system further includes a monitoring device that communicates glucose information to the controller, the glucose information being indicative of a blood glucose level of the user.

Certain embodiments described herein include a portable infusion pump system, which may include a portable pump housing that defines a space to receive medicine for dispensation to a user. The pump housing may at least partially house a pump drive system to dispense the medicine through a flow path to the user. The system may also include control circuitry that controls the pump drive system to dispense the medicine from the portable pump housing according to a closed-loop delivery mode in which insulin is dispensed, for example, at differing rates in response to feedback information of a user's blood glucose characteristic. The system may further include a user interface in communication with the control circuitry and being configured to receive user input to interrupt the closed-loop delivery mode. The control circuitry may be configured to temporarily interrupt the closed-loop delivery mode by dispensing from the infusion pump system a user-selected manual bolus dosage. Optionally, the control circuitry may be configured to automatically restart the closed-loop delivery mode after dispensation of the user-selected manual bolus dosage (or may be configured to automatically prompt the user to confirm (via a user interface display) the restarting the closed-loop delivery mode after dispensation of the user-selected manual bolus dosage).

Some or all of the embodiments described herein may provide one or more of the following advantages. First, some embodiments of the infusion pump system described herein can include a portable design that is configured to be conveniently worn by user (e.g., on the user's skin or in a pocket) while operating in closed-loop delivery mode so as to automatically adjust insulin dispensation to a user in response to the user's blood glucose level (or other physiological state).

Second, some embodiments of the infusion pump system may dispense insulin to a user in response to the user's blood glucose level while operating in a closed-loop delivery mode, yet the user can conveniently interrupt the closed-loop delivery mode for purposes of demanding manually-initiated bolus dosage. Such interruption of the closed-loop delivery mode may be a temporary interruption, for example, when the controller is configured to automatically return to the closed loop delivery mode after dispensation of the manually-initiated bolus dosage (without intervention from the user). Accordingly, the user can wear the infusion pump system that operates according to the closed-loop delivery mode throughout the day, but the user can briefly interrupt the closed-loop delivery mode to manually initiate a "meal bolus" (or other type of bolus) prior to consuming a meal. For example, the user may elect to manually enter a specific bolus dosage or to initiate the calculation of a suggested bolus dosage based upon user input of an estimated number of carbohydrates to be consumed. Because the user can manually initiate the user-prompted bolus dosage prior to consuming the meal (e.g., before the user's blood glucose level rises due to consuming the food), the user may not experience a significant rise in his or her blood glucose level that might otherwise occur if operating under closed-loop control. After the manually-initiated bolus dosage is dispensed to the user, the infusion pump system can be configured to automatically return to the closed-loop delivery mode.

Fourth, in some embodiments described herein, the infusion pump system can be configured to calculate a dosage amount for the manually-initiated bolus dosage that accounts not only for the user input (e.g., of an estimated number of carbohydrates or other parameters), but also accounts for the insulin that was previously dispensed (during the closed-loop delivery mode) but has not yet acted in the user's body. For example, the infusion pump system can determine a calculated dosage amount for the manually-initiated bolus dosage based upon both user input and an amount of insulin dispensed during the closed-loop delivery mode over a time period prior to the user-prompted bolus dosage. In doing so, some implementations of the infusion pump system may calculate the eIOB, which corresponds to the net amount of remaining active insulin in the user's system from dosages during the predetermined time period (e.g., including the various insulin dispensations that occurred during the closed-loop delivery mode).

Fifth, some embodiments of the infusion pump system may provide an additional level of safety to prevent an overdose of medicine resulting from a manually-initiated bolus dosage that interrupts a closed-loop delivery mode. For example, the infusion pump system may be configured to calculate a stacking value in response to receipt of a manually entered bolus dosage requested by the user. The stacking value may represent the amount of insulin that would be active in the user's body if the requested dosage were dispensed. If the stacking value exceeds a predetermined stacking threshold, the infusion pump system may attempt to prevent an overdose of the insulin by one or more of the following operations: alerting the user to the amount of eIOB, preventing dispensation of the requested dosage, and prompting the user to select a corrected dosage. The stacking value may be calculated by aggregating the requested bolus dosage with the eIOB.

Similarly, in some embodiments, the amount of eIOB can be accounted for in the calculation of a suggested bolus dosage prompted by the user. As another example, the infusion pump system may be configured to calculate a predicted future blood glucose level in response to receipt of a manually entered bolus dosage requested by the user. The future blood glucose level may represent a blood glucose level that is predicted to occur in the user's body as a result of the requested bolus dosage. If future blood glucose level falls below a predetermined minimum blood glucose level (e.g., a blood glucose level below which the user is likely to suffer symptoms of hypoglycemia, such as about 60 to 70 mg/dL in some cases), the infusion pump system may attempt to prevent an overdose of the insulin by one or more of the above-recited operations. The future blood glucose level may be calculated as the product of the stacking value and the user's insulin sensitivity.

Sixth, some embodiments of the infusion pump system can facilitate the controlled dispensation of both insulin and glucagon. For example, the infusion pump system may provide a suggested glucagon dosage based on one or more particular parameters (e.g., the user's recent blood glucose characteristics, food intake data, an amount of insulin and/or glucagon already delivered to the user which has not yet acted on the user, glucagon sensitivity of the user, and the like). The suggested glucagon dosage may be dispensed directly from the infusion pump device or manually injected via a suitable applicator (e.g., an injection pen). In some circumstances, a controller device of the infusion pump system can receive information indicative of the user's blood glucose level and suggest a glucagon dosage that is at least partially dependent upon a stored glucagon sensitivity value that is predetermined for the user. Such a glucagon dosage suggestion feature can be initiated, for example, by the infusion pump system in response to input of a blood glucose level that is below a target level, or in response to a predicted future low glucose event. In some implementations, the controller device may interrupt a closed-loop delivery mode to provide the suggested glucagon dosage, or, alternatively, facilitate the glucagon dosage "on top" of the closed-loop operations.

The details of one or more embodiments of the invention are set forth in the accompanying drawings and the description below. Other features, objects, and advantages of the invention will be apparent from the description and drawings, and from the claims.

DETAILED DESCRIPTION OF ILLUSTRATIVE EMBODIMENTS

Figure 1:
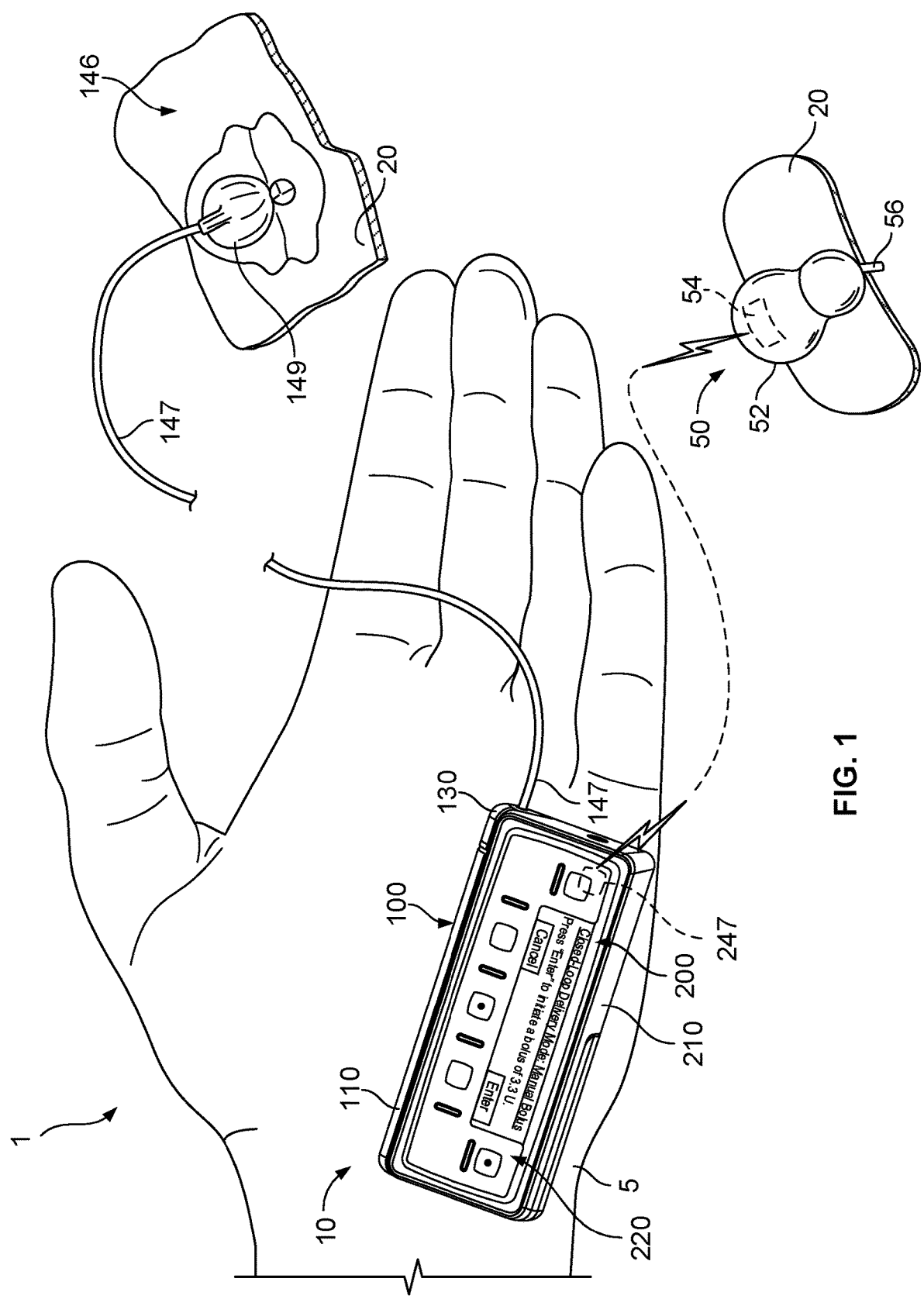
FIG. 1 is a perspective view of a first example infusion pump system, in accordance with some embodiments.

Referring to FIG. 1, some embodiments of an infusion pump system 1 can include a pump assembly 10 featuring a pump device 100 and a controller device 200. Optionally, the controller device 200 can be configured to releasably attach with the pump device 100. The controller device 200 can electrically communicate with the pump device 100 to control a drive system housed in the pump device 100 to dispense a medicine to a user (e.g., through a tube 147 of an infusion set 146 in this example). When the controller device 200 and the pump device 100 are assembled together, the user can (in some embodiments) conveniently wear the infusion pump system 1 on the user's skin under clothing, in a pouch clipped at the waist, or in the user's pocket while receiving the fluid dispensed from the pump device 100.

Briefly, in use, the pump device 100 in this embodiment is configured to removably attach to the controller device 200 in a manner that provides a secure fitting, an overall compact size, and a reliable electrical connection. For example, as described in more detail below in connection with FIG. 2, the controller device 200 can include a housing 210 having a number of features that mate with complementary features of the pump housing 110. In such circumstances, the controller device 200 can removably attach with the pump device 100 in a generally side-by-side configuration. The compact size permits the pump assembly 10 to be discrete and portable. The controller device 200 can receive user input for purposes of operating the infusion pump system 1. In some embodiments, as described further below in connection with FIGS. 4A-6B, the infusion pump system 1 can be configured (e.g., appropriately designed and programmed) to operate in a closed-loop delivery mode in which the controller device 200 operates the pump device 100 to dispense insulin to a user autonomously (e.g., without user interaction) based on a sensed physiological condition of the user. Optionally, the closed-loop delivery mode can be temporarily interrupted by the user to provide a manually-initiated bolus dosage (e.g., not an autonomous adjustment of the insulin dispensation). Preferably, the controller device 200 may automatically return to the closed-loop delivery mode following completion or termination of the manually-initiated bolus dosage. Once resumed, future operations of the closed-loop delivery mode can account for any insulin dispensed during the manually-initiated bolus dosage.

Still referring to FIG. 1, the infusion pump system 1 may optionally include a glucose monitoring device 50 in communication with the pump assembly 10 for the purpose of supplying data indicative of a user's blood glucose level to the controller device 200. In some embodiments, as described further below in connection with FIG. 5, the controller device 200 can utilize the data indicative of a user's blood glucose level during operations in the closed-loop delivery mode so as to autonomously adjust the insulin dispensation rate. The glucose monitoring device 50 can include a housing 52, a wireless communication device 54, and a sensor shaft 56. The wireless communication device 54 can be contained within the housing 52 and the sensor shaft 56 can extend outward from the housing 52. In use, the sensor shaft 56 can penetrate the skin 20 of a user to make measurements indicative of characteristics of the user's blood (e.g., the user's blood glucose level or the like). In response to the measurements made by the sensor shaft 56, the glucose monitoring device 50 can employ the wireless communication device 54 to transmit data to a corresponding wireless communication device 247 housed in the pump system 10. In some embodiments, the monitoring device 50 may include a circuit that permits sensor signals (e.g., data from the sensor shaft 56) to be communicated to the communication device 54. The communication device 54 can transfer the collected data to the controller device 200 (e.g., by wireless communication to the communication device 247). Alternatively, the monitoring device 50 can employ other suitable methods of obtaining information indicative of a user's blood characteristics and transferring that information to the controller device 200. For example, an alternative monitoring device may employ a micropore system in which a laser porator creates tiny holes in the uppermost layer of a user's skin, through which interstitial glucose is measured using a patch. In the alternative, the monitoring device can use iontophoretic methods to non-invasively extract interstitial glucose for measurement. In other examples, the monitoring device can include non-invasive detection systems that employ near IR, ultrasound or spectroscopy, and particular embodiments of glucose-sensing contact lenses. Invasive methods involving optical means of measuring glucose could also be added. In yet another example, the monitoring device can include an optical detection instrument that is inserted through the skin for measuring the user's glucose level.

Furthermore, it should be understood that in some alternative embodiments, the monitoring device 50 can be in communication with the controller device 200 via a wired connection. In other embodiments of the infusion pump system 1, one or more test strips (e.g., blood test strips) containing a sample of the user's blood can be inserted into a strip reader portion of the pump system 1 to be tested for characteristics of the user's blood. Alternatively, the test strips (e.g., glucose test strips) containing a sample of the user's blood can be inserted into a glucose meter device (not shown in FIG. 1), which then analyzes the characteristics of the user's blood and communicates the information (via a wired or wireless connection) to the controller device 200. In still other embodiments, characteristics of the user's blood glucose information can be entered directly into the pump system 10 via a user interface 220 on the controller device 200.

Figure 2:
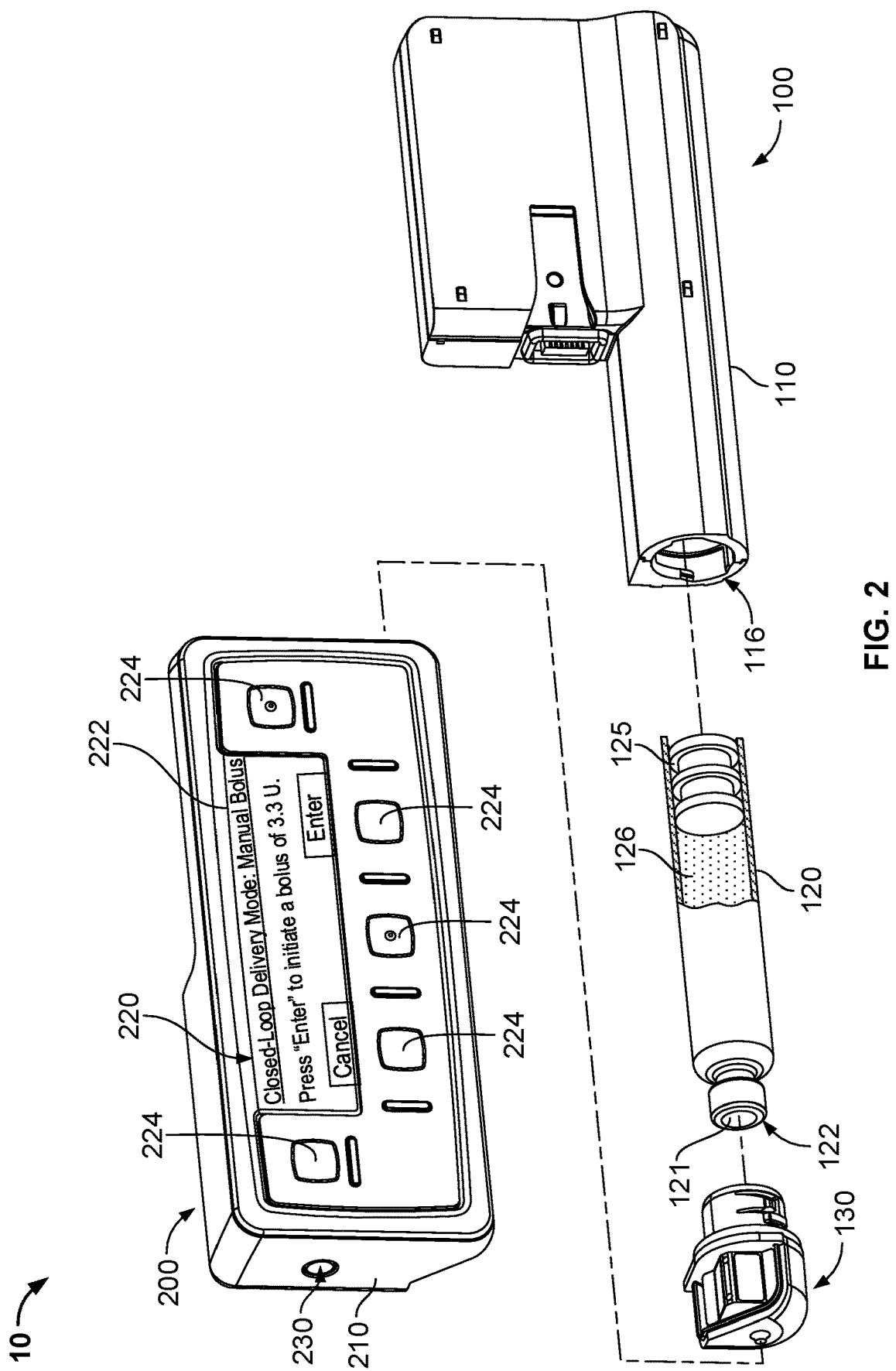
FIG. 2 is an exploded perspective view of a portion of the infusion pump system of FIG. 1.

Referring now to FIG. 2, the pump device 100 in this embodiment includes a housing structure 110 that defines a cavity 116 in which a fluid cartridge 120 can be received. The pump device 100 also can include a cap device 130 to retain the fluid cartridge 120 in the cavity 116 of the housing structure 110. The pump device 100 can include a drive system (not shown) that advances a plunger 125 in the fluid cartridge 120 so as to dispense fluid therefrom. In this embodiment, the controller device 200 communicates with the pump device 100 to control the operation of the drive system. Optionally, the controller device 200 may be configured as a reusable component that provides electronics and a user interface to control the operation of the pump device 100. In such circumstances, the pump device 100 can be a disposable component that is disposed of after a single use. For example, the pump device 100 can be a "one time use" component that is thrown away after the fluid cartridge 120 therein is exhausted. Thereafter, the user can removably attach a new pump device (having a new fluid cartridge) to the reusable controller device 200 for the dispensation of fluid from a new fluid cartridge. Accordingly, the user is permitted to reuse the controller device 200 (which may include complex or valuable electronics, as well as a rechargeable battery) while disposing of the relatively low-cost pump device 100 after each use. Such a pump assembly 10 can provide enhanced user safety as a new pump device (and drive system therein) is employed with each new fluid cartridge.

The pump assembly 10 can be a medical infusion pump assembly that is configured to controllably dispense a medicine from the cartridge 120. As such, the fluid cartridge 120 can contain a medicine 126 to be infused into the tissue or vasculature of a targeted individual, such as a human or animal patient. For example, the pump device 100 can be adapted to receive a fluid cartridge 120 in the form of a carpule that is preloaded with insulin or another medicine for use in the treatment of Diabetes (e.g., Byetta®, Symlin®, or others). Such a cartridge 120 may be supplied, for example, by Eli Lilly and Co. of Indianapolis, Ind. Other examples of medicines that can be contained in the fluid cartridge 120 include: pain relief drugs, hormone therapy, blood pressure treatments, anti-emetics, osteoporosis treatments, or other injectable medicines. The fluid cartridge 120 may have other configurations. For example, the fluid cartridge 120 may comprise a reservoir that is integral with the pump housing structure 110 (e.g., the fluid cartridge 120 can be defined by one or more walls of the pump housing structure 110 that surround a plunger to define a reservoir in which the medicine is injected or otherwise received).

In some embodiments, the pump device 100 can include one or more structures that interfere with the removal of the fluid cartridge 120 after the fluid cartridge 120 is inserted into the cavity 116. For example, the pump housing structure 110 can include one or more retainer wings (not shown) that at least partially extend into the cavity 116 to engage a portion of the fluid cartridge 120 when the fluid cartridge 120 is installed therein. Such a configuration may facilitate the "one-time-use" feature of the pump device 100. In some embodiments, the retainer wings can interfere with attempts to remove the fluid cartridge 120 from the pump device 100, thus ensuring that the pump device 100 will be discarded along with the fluid cartridge 120 after the fluid cartridge 120 is emptied, expired, or otherwise exhausted. In another example, the cap device 130 can be configured to irreversibly attach to the pump body 110 so as to cover the opening of the cavity 116. For example, a head structure of the cap device 130 can be configured to turn so as to threadably engage the cap device 130 with a mating structure along an inner wall of the cavity 116, but the head structure may prevent the cap device from turning in the reverse direction so as to disengage the threads. Accordingly, the pump device 100 can operate in a tamper-resistant and safe manner because the pump device 100 can be designed with a predetermined life expectancy (e.g., the "one-time-use" feature in which the pump device is discarded after the fluid cartridge 120 is emptied, expired, or otherwise exhausted).

Still referring to FIG. 2, the controller device 200 can be removably attached to the pump device 100 so that the two components are mechanically mounted to one another in a fixed relationship. In some embodiments, such a mechanical mounting can also form an electrical connection between the removable controller device 200 and the pump device 100. For example, the controller device 200 can be in electrical communication with a portion of the drive system (show shown) of the pump device 100. In some embodiments, the pump device 100 can include a drive system that causes controlled dispensation of the medicine or other fluid from the cartridge 120. In some embodiments, the drive system incrementally advances a piston rod (not shown) longitudinally into the cartridge 120 so that the fluid is forced out of an output end 122. A septum 121 at the output end 122 of the fluid cartridge 120 can be pierced to permit fluid outflow when the cap device 130 is connected to the pump housing structure 110. For example, the cap device 130 may include a penetration needle that punctures the septum 121 during attachment of the cap device to the housing structure 110. Thus, when the pump device 100 and the controller device 200 are mechanically attached and thereby electrically connected, the controller device 200 communicates electronic control signals via a hardwire-connection (e.g., electrical contacts or the like) to the drive system or other components of the pump device 100. In response to the electrical control signals from the controller device 200, the drive system of the pump device 100 causes medicine to incrementally dispense from the fluid cartridge 120. Power signals, such as signals from a battery (not shown) of the controller device 200 and from the power source (not shown) of the pump device 100, may also be passed between the controller device 200 and the pump device 100.

The controller device 200 can include a user interface 220 that permits a user to monitor and actively control the operation of the pump device 100. In some embodiments, the user interface 220 can include a display device 222 and one or more user-selectable buttons (e.g., several buttons 224 are shown in the embodiment of FIGS. 1-2). The display device 222 can include an active area in which numerals, text, symbols, images, or a combination thereof can be displayed. For example, the display device 222 can be used to communicate a number of settings or menu options for the infusion pump system 1 (FIG. 1). In this embodiment, the user may press one or more of the buttons to shuffle through a number of menus or program screens that show particular operational modes (e.g., closed-loop delivery mode and, optionally, an open-loop delivery mode in which a basal profile is implemented and then supplemented with user-selected bolus dosages), settings (e.g., dosage parameters) and data (e.g., review data that shows a medicine dispensing rate, a total amount of medicine dispensed in a given time period, an amount of medicine scheduled to be dispensed at a particular time or date, an approximate amount of medicine remaining in the cartridge 120, or the like). In some embodiments, the user can adjust the modes and/or settings, or otherwise program the controller device 200 by pressing one or more buttons 224 of the user interface 220. For example, the user may press one or more of the buttons to temporarily change the operation of the infusion pump system 1 from a closed-loop delivery mode to provide at least one manually-initiated bolus dosage. In some implementations, the display device 222 may also be used to communicate information regarding remaining battery life.

The controller device 200 can also be equipped with an inspection light device 230. The inspection light device 230 can provide the user with a tool to illuminate and inspect a targeted location. For example, the inspection light device 230 can be directed at the infusion site on the user's skin to verify that the infusion set is properly embedded, or the inspection light device 230 can be directed at the pump device 100 to illuminate the cavity 116 or other areas. The inspection light device 230 can also be used to notify the user to an alert condition of the pump system 10. For example, as described in more detail below, the inspection light device 230 can be activated when the controller has detected a possible problem with the infusion set 146. An activation of the inspection light device 230 can thereby provide a visual notification (as an alternative to, or in addition to, the visual notification provided on the display device 222) to the user that attention to the pump system 10 is warranted.

The pump assembly 10 can be configured to be portable and can be wearable and concealable. For example, a user can conveniently wear the pump assembly 10 on the user's skin (e.g., skin adhesive) underneath the user's clothing or carry the pump device 100 in the user's pocket (or other portable location) while receiving the medicine dispensed from the pump device 100. The pump assembly 10 is depicted in FIG. 1 as being held in a user's hand 5 so as to illustrate its size in accordance with some embodiments. This embodiment of the pump assembly 10 is compact so that the user can wear the portable pump assembly 10 (e.g., in the user's pocket, connected to a belt clip, adhered to the user's skin, or the like) without the need for carrying and operating a separate module. In such embodiments, the cap device 130 of the pump device 100 can be configured to mate with an infusion set 146. As shown in FIG. 1, the infusion set 146 can be a tubing system that connects the pump assembly 10 to the tissue or vasculature of the user (e.g., to deliver medicine into the tissue or vasculature under the user's skin). The infusion set 146 can include a flexible tube 147 that extends from the pump device 100 to a subcutaneous cannula 149 that may be retained by a skin adhesive patch (not shown) that secures the subcutaneous cannula 149 to the infusion site on the user's skin 20. The skin adhesive patch can retain the infusion cannula 149 in fluid communication with the tissue or vasculature of the user so that the medicine dispensed through the tube 147 passes through the cannula 149 and into the user's body. The cap device 130 can provide fluid communication between the output end 122 (FIG. 2) of the fluid cartridge 120 and the tube 147 of the infusion set 146.

In some embodiments, the pump assembly 10 can be pocket-sized so that the pump device 100 and controller device 200 can be worn in the user's pocket or in another portion of the user's clothing. In some circumstances, the user may desire to wear the pump assembly 10 in a more discrete manner. Accordingly, the user can pass the tube 147 from the pocket, under the user's clothing, and to the infusion site where the adhesive patch can be positioned. As such, the pump assembly 10 can be used to deliver medicine to the tissues or vasculature of the user in a portable, concealable, and discrete manner.

In some embodiments, the pump assembly 10 can be configured to adhere to the user's skin directly at the location in which the skin is penetrated for medicine infusion. For example, a rear surface of the pump device 100 can include a skin adhesive patch so that the pump device 100 can be physically adhered to the skin of the user at a particular location. In these embodiments, the cap device 130 can have a configuration in which medicine passes directly from the cap device 130 into an infusion cannula 149 that is penetrated into the user's skin. In some examples, the user can temporarily detach the controller device 200 (while the pump device 100 remains adhered to the skin) so as to view and interact with the user interface 220.

Figure 3:
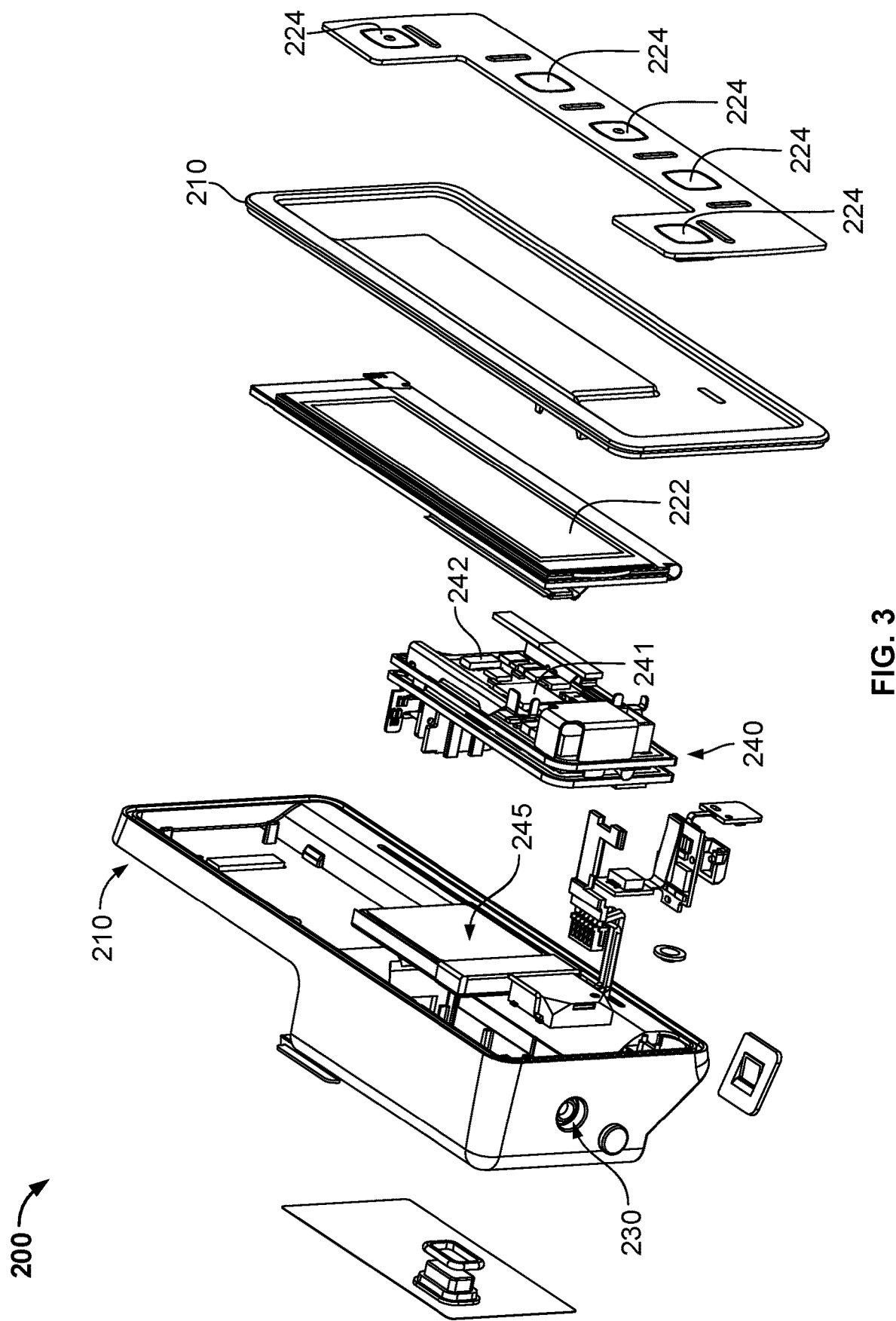
FIG. 3 is an exploded perspective view of a controller device for the infusion pump system of FIG. 1.

Referring now to FIG. 3, the controller device 200 (shown in an exploded view) houses a number of components that can be reused with a series of successive pump devices 100. In particular, the controller device 200 can include control circuitry 240 and a rechargeable battery pack 245, each arranged in the controller housing 210. The rechargeable battery pack 245 may provide electrical energy to components of the control circuitry 240, other components of the controller device (e.g., the display device 222 and other user interface components, sensors, or the like), and/or to components of the pump device 100. The control circuitry 240 may be configured to communicate control or power signals to the drive system of the pump device 100, or to receive power or feedback signals from the pump device 100.

The control circuitry 240 of the controller device 200 can include one or more microprocessors 241 configured to execute computer-readable instructions stored on one or more memory devices 242 so as to achieve any of the control operations described herein. For example, at least on memory device 242 of the control circuitry 240 may be configured to store computer-readable instructions for operating the pump device 100 according to a closed-loop delivery mode and an open-loop delivery mode.

In the closed-loop delivery mode, the control circuitry 240 of the controller device 200 can operate the pump device 100 to autonomously alter the dispensation of insulin to a user based upon a sensed physiological condition of the user. For example, if the infusion pump system is dispensing insulin, closed-loop operations facilitated by the control circuitry may cause the infusion pump system to imitate a pancreatic beta cell so that the insulin dispensation is adjusted according to increases or decreases in the user's blood glucose level (see FIG. 5). This type of closed-loop control can be executed by the control circuitry via any suitable control algorithm (e.g., a proportional-integral-derivative (PID), fuzzy logic, or model predictive control algorithm). For example, U.S. Pat. No. 8,548,544 provides various examples of suitable closed-loop techniques involving fuzzy logic and predictive models for automated insulin dispensation.

Additionally, as described herein, even when the controller device 200 is operating in the closed-loop delivery mode, the user can choose to temporarily interrupt the closed-loop delivery mode for purposes of demanding manually-initiated bolus dosage. In such circumstances, the user can advantageously wear the infusion pump system 1 that operates according to the closed-loop delivery mode throughout the day, but the user can briefly interrupt the closed-loop delivery mode to manually initiate a "meal bolus" (or other type of bolus). For example, the user can trigger (via the user interface 220) an interruption of the closed-loop delivery mode, so that the user can manually enter a specific bolus dosage or initiate the calculation of a suggested bolus dosage based upon user input of an estimated number of carbohydrates to be consumed. Because the user can manually initiate the user-prompted bolus dosage prior to consuming the meal (e.g., before the user's blood glucose level rises due to consuming the food), the user may not experience a significant rise in his or her blood glucose level that might otherwise occur if operating under closed-loop control. After the manually-initiated bolus dosage is dispensed to the user, the infusion pump system can be configured to automatically return to the closed-loop delivery mode.

In the open-loop delivery mode, the control circuitry 240 of the controller device 200 can operate the pump device 100 to deliver insulin to the user according to a basal rate profile and user-selected bolus dosages. The user may select one or more bolus deliveries, for example, to offset the blood glucose effects caused by food intake, to correct for an undesirably high blood glucose level, to correct for a rapidly increasing blood glucose level, or the like. In some examples, the bolus dosages can be determined based on calculations made by the controller device 200 in response to a request by the user. For example, when the user's blood glucose level is rapidly increasing and has reached a high level (e.g., as indicated by the data received from the glucose monitoring device 50), the user may request the controller device 200 to calculate an appropriate bolus dosage of insulin to correct for the rapid increase and elevated blood glucose level. In another example, the user can request (via the user interface 220) that the controller device 200 calculate and suggest a bolus dosage based, at least in part, on a proposed meal that the user plans to consume.

The insulin dispensed into the user's body during closed-loop delivery mode and during any manually-initiated bolus dosages may act over a period of time to control the user's blood glucose level. As such, the user can benefit from the embodiments of the infusion pump system 1 that can take into account different circumstances and information when determining a dosage amount. For example, when calculating an insulin dosage, the controller device 200 employed one or more user-specific dosage parameters that reflect the user's physiological response to insulin. In some embodiments, the controller device 200 can employ the user-specific dosage parameters in combination with data indicative of the user's blood glucose level, historical food intake data previously submitted by the user, the user's insulin load, and the like to provide an accurate dosage calculation. Exemplary information that can be derived from the user's blood glucose information that can be used by the controller device 200 in determining a bolus dosage can include the user's current blood glucose level, the rate of change in the user's blood glucose level, the 2nd derivative of the user's blood glucose data, the shape and/or appearance of the user's blood glucose curve, or the like. In some embodiments, the controller device 200 can use information from previously entered meals and previously delivered insulin dosages when calculating a suggested bolus dosage. In these embodiments, information regarding previously entered meals and previously delivered insulin dosages from 12 hours or more (e.g., 24 hours, 12 hours, 8 hours, 6 hours, 0.5 hours, or the like) can be used in the bolus dosage calculations.

Relevant user-specific dosage parameters may include, but are not limited to, one or more of the following: insulin sensitivity (e.g., in units of mg/dL/insulin unit), carbohydrate ratio (e.g., in units of g/insulin unit), insulin onset time (e.g., in units of minutes and/or seconds), insulin-on-board duration (e.g., in units of minutes and/or seconds), and basal rate profile (e.g., an average basal rate or one or more segments of a basal rate profile expressed in units of insulin unit/hour). These and other suitable dosage parameters may be pre-loaded into the control circuitry 240 or input by a user via the user interface. Further, in some examples, the control circuitry 240 can cause the memory device 242 to store any of the following parameters derived from the historical pump usage information: dosage logs, average total daily dose, average total user-initiated bolus dose per day, a ratio of correction bolus amount per day to food bolus amount per day, amount of correction boluses per day, a ratio of a correction bolus amount per day to the average total daily dose, average maximum bolus per day, and a frequency of cannula and tube primes per day. To the extent these aforementioned dosage parameters or historical parameters are not stored in the memory device 241, the control circuitry 240 can be configured to calculate any of these aforementioned dosage parameters or historical parameters from other data stored in the memory device 241 or otherwise input via the user interface 220.

The user interface 220 of the controller device 200 can include input components and/or output components that are electrically connected to the control circuitry 240. For example, the user interface 220 can include the display device 222 having an active area that outputs information to a user and buttons 224 that the user can use to provide input. Here, the display device 222 can be used to communicate a number of settings (e.g., user-specific dosage parameters) or menu options (e.g., options for interrupting a closed-loop delivery mode to provide a manually-initiated bolus dosage) for the infusion pump system 1. In some embodiments, the control circuitry 240 can receive input commands from a user's button selections and thereby cause the display device 222 to output a number of menus or program screens that show particular settings and data. The control circuitry 240 may be programmable to cause the control circuitry 240 to change any one of a number of settings or modes of operation for the infusion pump system 1. In some embodiments, the control circuitry 240 can include a cable connector (e.g., a USB connection port or another data cable port) that is accessible on an external portion of the controller housing 210. As such, a cable can be connected to the control circuitry 240 to upload or download data or program settings to the control circuitry.

Figure 4A:
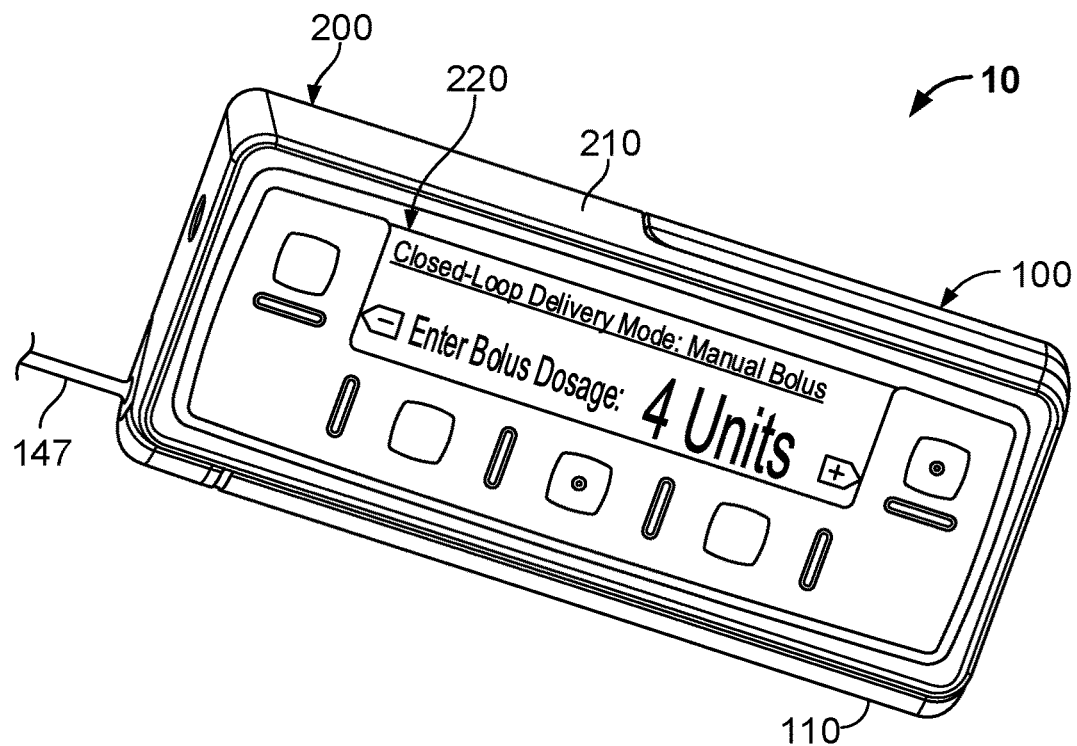
FIG. 4A is a perspective view of the infusion pump system of FIG. 1 including a user interface display for inputting a manual bolus dosage, in accordance with some embodiments.
Figure 4B:
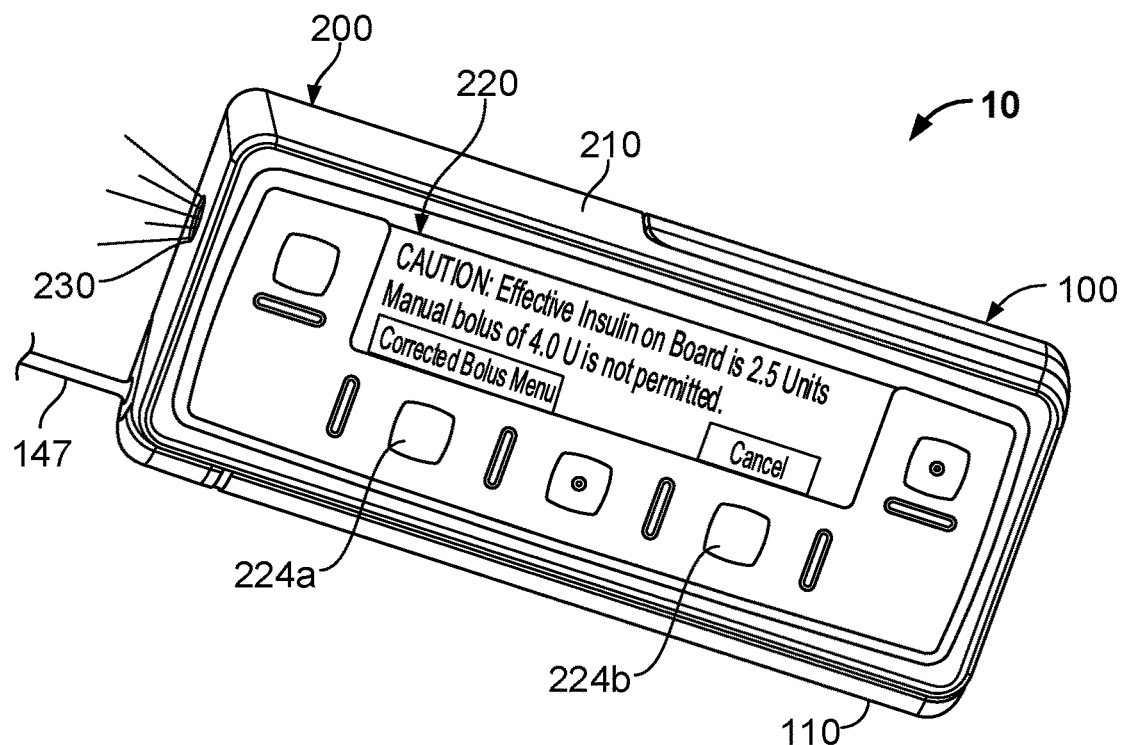
FIG. 4B is a perspective view of the infusion pump system of FIG. 1 including a user interface display for outputting an alert indicating a manual bolus dosage is not permitted.
Figure 4C:
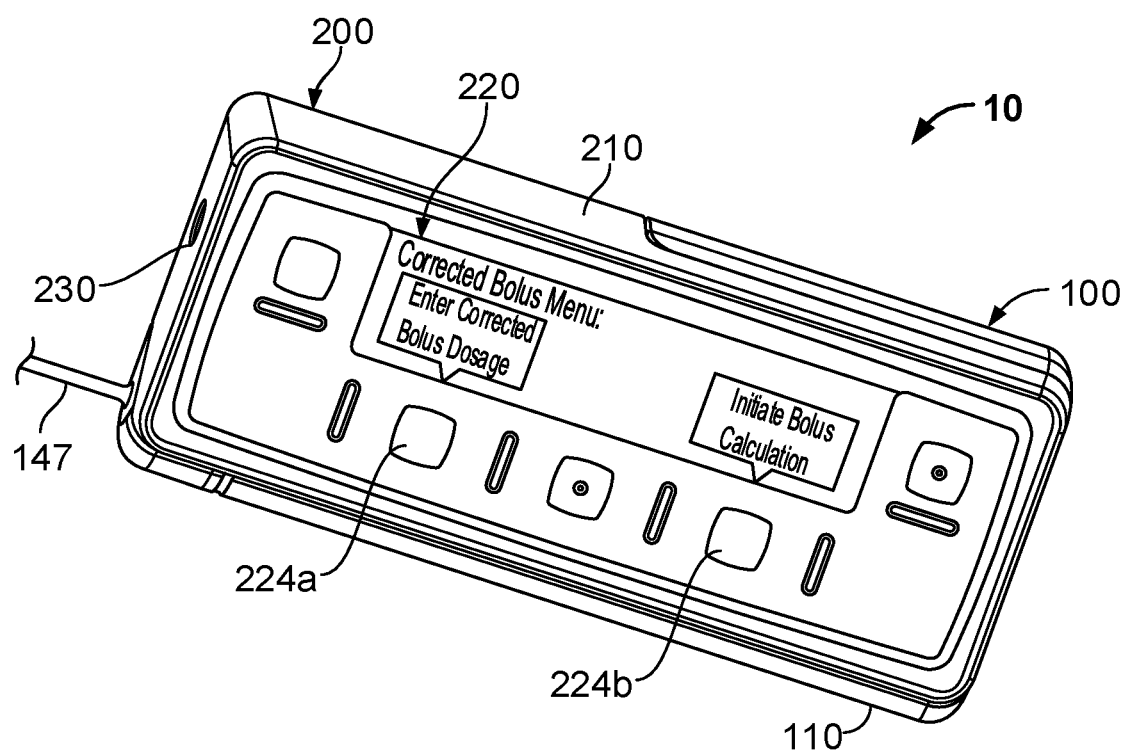
FIG. 4C is a perspective view of the infusion pump system of FIG. 1 including a user interface display for providing menu options to correct the non-permitted manual bolus dosage.

Referring now to FIGS. 4A-4C, the controller device 200 of the pump assembly 10 can be configured to receive user input triggering a temporary interruption of a closed-loop delivery mode of operations. For example, the user interface 220 can be employed to manually input a desired bolus dosage (e.g., in anticipation of a meal or to manually correct a high blood glucose level). As shown in FIG. 4A, the user may activate particular buttons 224 of the user interface 220 so as to select a particular menu option that prompts the user to input a value for the bolus dosage in terms of insulin units. Some examples of temporarily interrupting the closed-loop delivery mode to provide a manually-initiated bolus dosage are explained in further detail below in connections with FIGS. 5 and 6A-B. Optionally, in this embodiment depicted in FIGS. 4A-C, the controller device 200 can receive the bolus dosage value selected by the user and determine whether the requested bolus dosage may undesirably "stack" with previous dosages to cause an overdose of insulin (e.g., symptoms of hypoglycemia). Thus, for example, the controller device 200 may calculate a "stacking value" accounting for insulin previously delivered to the user during the closed-loop delivery mode of the pump assembly 10 in addition to the requested dosage entered by the user. In some implementations, the stacking value is calculated by aggregating the bolus dosage requested by the user together with the "effective insulin-on-board" (eIOB). The eIOB corresponds to the net amount of remaining active insulin in the user's system over a selected time period immediately prior to the calculation. One non-limiting example is described below:

$$\text{Stacking Value} = (\text{Requested Bolus Dosage}) + (\text{eIOB}).$$

$$\text{eIOB} = [\Sigma(\text{Dosage}_n * \text{Duration Factor}(t)_n)] - \text{Estimated Basal Rate},$$

where $\text{Dosage}_n$ represents the quantity of any insulin dosage among "n" number of dosages delivered to the user during the selected time period ("n" being any positive whole number), where $\text{Duration Factor}(t)_n$, represents a factor discounting the dosage based on the amount of time "t" since its delivery, and where Estimated Basal Rate represents an estimate of the user's background insulin needs.

Due in part to pharmacokinetic effects (e.g., the time it takes for insulin to enter the blood stream from the subcutaneous point of delivery) and pharmacodynamic effects (e.g., the time it takes for a concentration of insulin in the blood to have the physiological effect of lower blood glucose level), insulin dispensed into the user's system may not act instantaneously, but instead may act over a period of time to control the user's blood glucose level. As such, at any given time the user's body may include some amount of insulin that has not yet acted. Thus, a duration factor determined as a function of time is applied to the quantity of each dosage during the specified time period to estimate a value of previously dispensed insulin that has not yet acted in the user's body. In some implementations, suitable duration factors may be determined based on a duration of action profile preloaded into the controller device 200. In some implementations, suitable duration factors may be calculated on demand by the controller device 200 based on historical logs of previous dosages and blood glucose data stored in computer memory.

As previously described, the pump controller 200 can optionally operate in an open-loop mode where scheduled basal dosages of insulin are supplied in addition to user-prompted bolus dosages. The basal delivery rate can be selected to maintain a user's blood glucose level in a targeted range during normal activity when the user is not consuming food items. Thus, the basal delivery rate may correspond to the user's background insulin needs. In the open-loop delivery mode, the user-selected bolus deliveries supplement the scheduled basal deliveries by providing substantially larger amounts of insulin in particular circumstances, such as when the user consumes food items, when the user's blood glucose level increases beyond a safe limit, when the user's blood glucose level rises faster than a threshold rate, or other scenarios in which the blood glucose level requires a significant correction.

When the infusion pump system 1 operates in a closed-loop mode, however, the insulin dispensation is autonomously adjusted in response to changes in the user's blood glucose level. As such, in the closed-loop mode, the infusion pump system 1 may not necessarily adhere to a pre-stored basal schedule (because the user's blood glucose level is changing). Thus, the user's background insulin needs cannot simply be taken as a constant, pre-stored basal delivery rate, but the controller device 200 may instead approximate an "Estimated Basal Rate" based on the insulin dispensations performed during the closed-loop delivery mode. The estimated basal rate may be preloaded into the controller device or calculated based on historical logs of previous insulin dosages and/or user input (e.g., user input indicating a total daily dose of insulin). In some embodiments, the estimated basal rate may calculated as:

Estimated Basal Rate=Total Dose/($T$*Scale Down Factor), where Total Dose represents the quantity of insulin delivery during the time period "T", and where Scale Down Factor represents a multiplier selected to scale down the total dose to a fractional value that only accounts for insulin delivered to meet the user's background insulin needs.

For example, if the time period "T" is taken as 24 hours and the scale down factor is taken as 2.0, the estimated basal rate is calculated as the total daily dose divided by 48.0, which corresponds to the hourly rate needed to provide 50% of the total daily dose as basal insulin for fulfilling the user's background insulin needs. In some embodiments, the scale down factor can range from about 2.50 to about 1.50 (e.g., about 1.66).

In some embodiments, the estimated basal rate may be determined by calculating the average basal rate outside of detectable meal times for a given time period. More specifically, the controller device 200 may exclude insulin deliveries adjacent detected meal times from the average basal rate calculation. For example, the controller device 200 may exclude insulin delivers from a predetermined time before (e.g., 0 to 45 minutes) and after (e.g., 90 to 180 minutes) a detected meal from the average basal rate calculation. Any suitable meal-detection algorithm can be used for determining an estimated basal rate according to the above described technique. In some embodiments, a fuzzy-logic dosing rules matrix can be used to determine when meals have occurred. For example, certain cells of the matrix may be pre-set as associated with basal or meal-time bolus insulin; and/or statistical analytics may be employed to identify cells that tend to correspond with the onset of glucose rise after a meal for a particular user. Further, in some embodiments, the controller device 200 may determine that a meal has taken place based on direct scrutiny of the user's blood glucose level. For example, a rapid increase in blood glucose may signal that a meal is likely to have taken place.

In some embodiments, insulin delivers adjacent detectable exercise sessions may be excluded from the estimated basal rate calculation. For example, in some embodiments, activity sensors incorporated within the infusion pump system 1 or linked via telemetry could be used to identify exercise or elevated activity levels. Typically the need for insulin is reduced following exercise. Thus excluding insulin delivery data for a period of time after the detection of elevated activity would improve the detection of underlying basal delivery. As one particular, non-limiting example, after detecting 45 minutes of activity levels related to running or walking, the system could be designed to exclude insulin deliveries from the estimated basal calculation for a period of 2 to 8 hours.

As shown in FIG. 4B, if the value input by the user causes the stacking value to exceed a predetermined stacking threshold, the controller device 200 can output an alert to the user in the form of a textual alert message provided on the display device 222 and, optionally, an audible or vibratory alarm and a temporary illumination of the aforementioned flashlight instrument 230. In this example, the textual alert notifies the user of the amount eIOB and indicates that the manually entered bolus dosage is not permitted. In addition to providing the alert, the controller device 200 may also prompt the user to take a corrective action. For example, the user can select a button 224a causes the controller device 200 to respond by displaying various menu options to correct the non-permitted manual bolus dosage (e.g., an option to re-enter a corrected bolus dosage and an option to initiate a suggested bolus calculation, see FIG. 4C). Alternatively, the user can select a button 224b indicating that the user does not wish to continue with a manual bolus dosage, allowing the controller device 200 to cancel the attempt to initiate a manual bolus and thereby resume closed-loop delivery mode.

Figure 5:
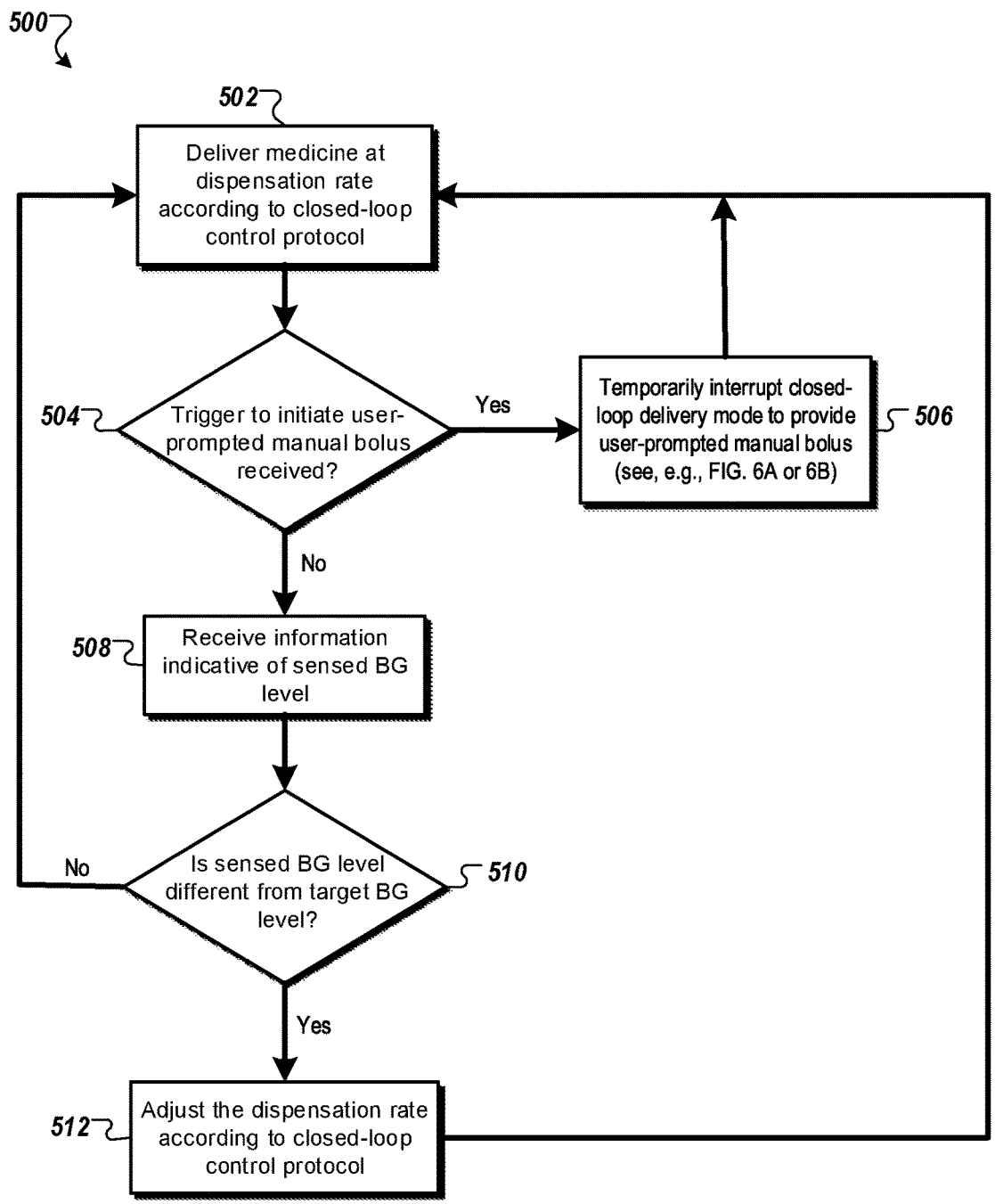
FIG. 5 is a flowchart of an example process for operating an infusion pump system an interruptible closed-loop mode of control, in accordance with some embodiments.

Referring now to FIG. 5, the control circuitry of an infusion pump system can implement a process 500 of operating the infusion pump system according to an interruptible closed-loop mode of control. Such a process 500, for example, can be implemented by the control circuitry 240 housed in the controller device 200 of an infusion pump assembly 10 (FIGS. 1-3). However, the description here is not necessarily limited to any particular infusion pump system with respect to process 500, and the process 500 may be implemented using, for example, an infusion pump system in which the control circuitry and drive system components are housed together in a reusable pump unit (see FIG. 7).

In operation 502, the controller device 200 delivers medicine (e.g., insulin in this embodiment) at a dispensation rate according to a closed-loop control protocol. As previously described, in the embodiments in which the infusion pump system is dispensing insulin, closed-loop operations facilitated by the control circuitry may cause the infusion pump system to imitate a pancreatic beta cell so that the insulin dispensation is adjusted according to increases or decreases in the user's blood glucose level (see FIG. 5). This type of closed-loop control (often termed "artificial pancreas control") can be executed by the control circuitry via any suitable control algorithm (e.g., a proportional-integral-derivative (PID), fuzzy logic, or model predictive control algorithm).

In operation 504, the controller device 200 can detect receipt of a trigger to initiate a user-prompted bolus dosage. Such a trigger can occur at any time during the closed-loop delivery mode. As previously described, in some embodiments, such a trigger event may include a user's selection of a particular button (e.g., a physical button or a touchscreen button) on the user interface of the controller, which may indicate the user's request for a manually-initiated bolus dosage. In operation 506, if the trigger is received (504), the controller device 200 can temporarily interrupt the closed-loop delivery mode to provide the user-prompted manual bolus (see FIGS. 6A and 6B) and then automatically returns to the closed-loop delivery mode at operation 502.

When no trigger is detected (504), the process 500 continues in the closed loop delivery mode. In operation 508, the pump system can receiving blood glucose information indicative of a sensed blood glucose level of the user. For example, as described above, blood glucose data can be received from a glucose monitoring device 50 in wireless communication with the pump assembly 10 (or received from a blood glucose test strip reader).

In operation 510, the sensed blood glucose level (as indicated by the received blood glucose data) is compared to a target blood glucose level (or otherwise compared to a target blood glucose range). In one implementation, one or more target blood glucose levels may be stored in memory device 242 of the control circuitry 240. The target blood glucose levels may correspond to one or more monitored sensory feedback signals. For instance, the target blood glucose level may vary according to the user's food intake and/or physiological status. As one example, the member device 242 stores data indicating at least a fasting target blood glucose level and a postprandial target blood glucose level. In some embodiments, a target blood glucose level can be expressed as a range. In some embodiments, the target blood glucose levels can be manually submitted to the controller device 200 via the user interface 220. In some embodiments, the target blood glucose levels can be determined statistically or empirically by the controller device 200 as a user-specific dosage parameter based on previous iterations of a closed-loop delivery scheme.

If operation 510 reveals that the sensed blood glucose level is different from the targeted blood glucose level, the process 500 continues to operation 512 so that the dispensation rate is autonomously adjusted according to the closed-loop control protocol. In some embodiments, the dispensation rate is adjusted according to PID control calculations, fuzzy logic control calculations, and/or model predictive control calculations. Then, the controller device 200 returns to operation 502 so that the medicine is dispensed at the newly adjusted dispensation rate while awaiting detection of a trigger (operation 504) and/or updated information indicative of a sensed blood glucose level (operation 508).

If operation 510 reveals that the sensed blood glucose level is not different from the targeted blood glucose level, the process 500 returns to operation 502 so that the medicine is dispensed at the previously implemented dispensation rate while awaiting detection of a trigger (operation 504) and/or updated information indicative of a sensed blood glucose level (operation 508).

As noted above, a suitable closed-loop delivery mode may also be implemented via predictive control techniques. For example, one or more predictive models or fuzzy-logic dosage matrices may be employed to drive the dispensation of insulin dosages based on predicted blood glucose levels, such as described in U.S. Pat. No. 8,548,544.

In some implementations, one or more processes or specific operations described herein can be used in conjunction with types of medication other than insulin—e.g., glucagon. The glucagon may be delivered to a user via an infusion pump device or injected using a manual syringe or a single use injection "pen." In some circumstances, an injectable form of glucagon is used in emergency aid of severe hypoglycemia when the victim is unconscious or for other reasons cannot take glucose orally. The glucagon fluid can be rapidly injected to the patient by intramuscular, intravenous or subcutaneous injection, and quickly raises the blood glucose level of the patient.

Figure 6A:
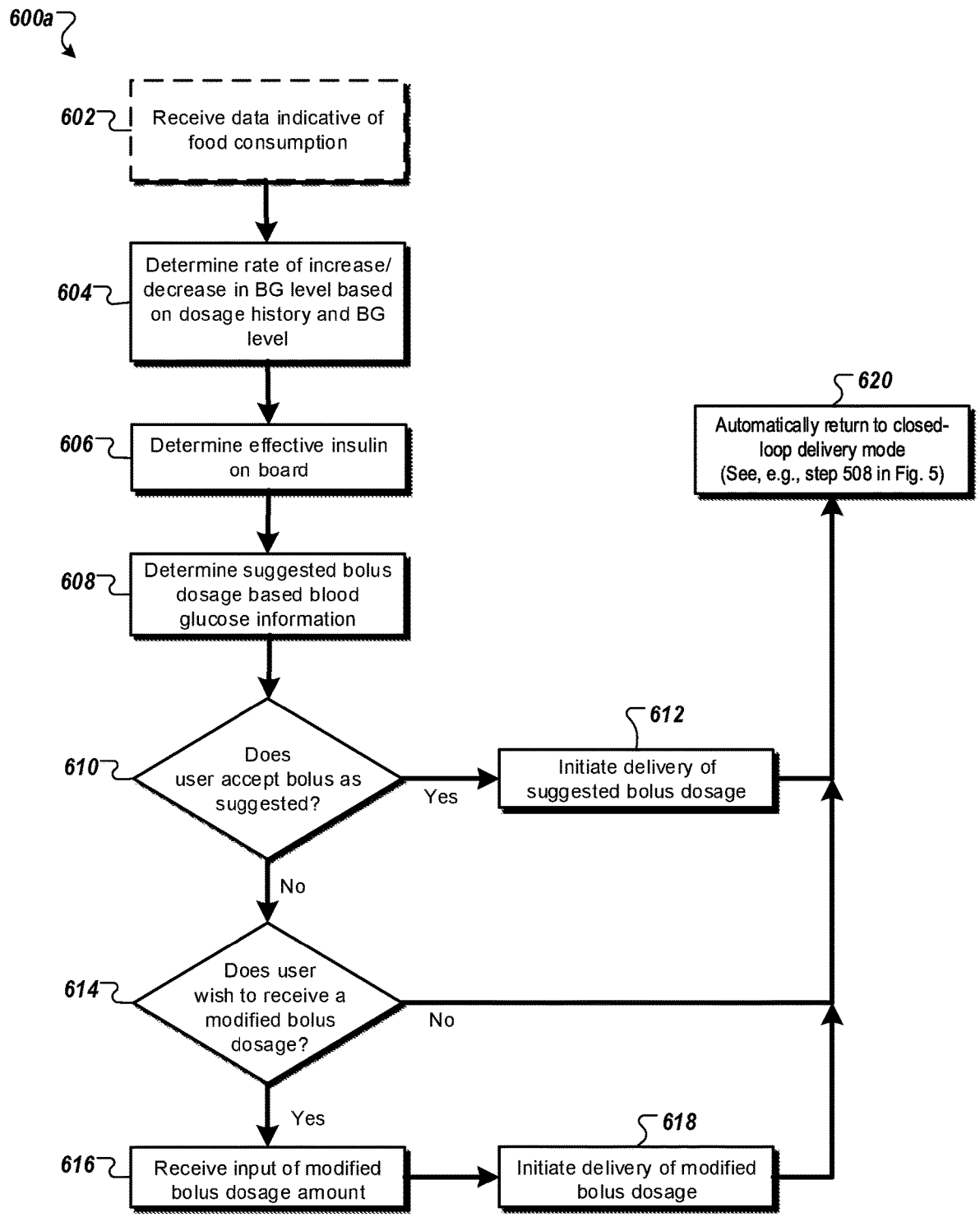
FIG. 6A is a flowchart of a first example process for temporarily interrupting a closed-loop delivery mode for providing a manually-initiated bolus dosage, in accordance with some embodiments.

FIG. 6A depicts a first example process 600a for interrupting the closed-loop delivery mode to provide a manually-initiated bolus dosage, for example, where medicine dosages (e.g., bolus dosages of insulin) are calculated in response to a request by the user and/or suggested by the controller device and confirmed by the user. In some embodiments, the controller device 200 may implement one or more operations of the process 600a to determine and suggest an insulin bolus dosage which includes a food offsetting component, a blood glucose correction component, and an eIOB component. The food offsetting component can represent an insulin bolus dosage to offset food intake data that have not previously been offset by an earlier bolus dosage. The blood glucose correction component can represent an insulin bolus dosage to maintain or return the user's blood glucose level to a targeted value within a predetermined range. This component can be derived from one or more dosage parameters (e.g., insulin sensitivity and carbohydrate ratio), data indicative of a user's blood glucose level (e.g., the user's current blood glucose level) and the recent rate of change in the user's blood glucose level. As described above, the eIOB component corresponds to the net amount of remaining active insulin in the user's system over a selected time period immediately prior to the calculation. In some embodiments, the suggested bolus dosage value can be calculated based on at least two of the three components as previously described: the food offsetting component and/or the blood glucose correction component combined with the eIOB component. It should be understood from the description herein that the components can be contemporaneously calculated to provide the suggested bolus dosage value or, alternatively, calculated in discrete steps and then combined to provide the suggested bolus dosage value.

Referring in more detail to FIG. 6A, in operation 602, the user can optionally enter data indicative of food intake (e.g., a meal that is about to be consumed, a meal that has recently been consumed, or the like) using the user interface 220 of the controller device 200. In operation 604, the controller device 200 can determine a rate of change (e.g., increase or decrease) based on the dosage history and the blood glucose level. In operation 606, the controller device 200 determines the eIOB.

After the user's blood glucose information is obtained (e.g., via operations 602-606), in operation 608, the controller device 200 can determine a suggested bolus dosage based on the obtained data and the user-specific dosage parameters that were determined during the closed-loop delivery mode. As noted above, in some embodiments, the suggested bolus dosage value can be calculated by the controller device 200 based on the eIOB component and one or both of the food offsetting component and the blood glucose correction component. In such embodiments, the food offsetting component can represent an insulin bolus dosage to offset food intake data that have not previously been offset by an earlier bolus dosage. The blood glucose correction component can represent an insulin bolus dosage to maintain or return the user's blood glucose level to a targeted value within a predetermined range. The eIOB component can take into account the net amount of remaining active insulin in the user's system over a selected time period immediately prior to the calculation. One non-limiting example is described below:

Suggested Bolus Dosage=(Food Offsetting Component)+(Blood Glucose Correction Component)−(eIOB Component).

Food Offsetting Component=(Carbohydrate Intake)*(Insulin to Carb. Ratio), where Carbohydrate Intake represents the number of grams of carbohydrates consumed (or to be consumed) and Insulin to Carb. Ratio represents a user-specific ratio (which was preferably determined and stored during the closed-loop mode during this embodiment) of the amount of insulin required to offset the consumption of a gram of carbohydrates (e.g., 14.8 U/g or the like).

Blood Glucose Correction Component=(Current Blood Glucose Level−Target Glucose Level)*Insulin Sensitivity, where Current Blood Glucose Level represents the most recent blood glucose level, Target Glucose Level represents the user's desired blood glucose level, Insulin Sensitivity represents a user-specific value (which was preferably determined and stored during the closed-loop mode during this embodiment) that correlates the number of units of insulin required to alter the user's blood glucose level by 1 mg/dL.

eIOB Component=[Σ(Dosage$_n$*Duration Factor($t$)$_n$)]−Estimated Basal Rate, where Dosage$_n$ represents the quantity of any insulin dosage among "n" number of dosages delivered to the user during the selected time period ("n" being any positive whole number), where Duration Factor(t)$_n$ represents a factor discounting the dosage based on the amount of time "t" since its delivery, and where Estimated Basal Rate represents an estimate of the user's background insulin needs.

In operation 610, the controller device 200 can determine if the user accepts the suggested bolus dosage. For example, the user can select the user interface button 224 corresponding to the "YES" or "NO" option presented on the display device 222 to accept or decline the suggested bolus dosage. In operation 612, if the accepts the suggested bolus dosage (610), the controller device 200 can initiate delivery of the suggested bolus dosage by the pump device 100. If the user declines the suggested bolus dosage (610), the controller device 200 can prompt the user for a modified dosage. In operation 614, the controller device 200 can determine if the user wishes to receive a modified bolus dosage. In operation 616, if the user wishes to receive a modified bolus dosage (614), the controller device 200 can obtain the modified bolus dosage. For example, the user can enter a modified bolus dosage or provide additional data that can be used to calculate a modified dosage via the user interface 220. In operation 618, the controller device 200 can initiate delivery of the modified bolus dosage by the pump device 100. After a suggested (612) or modified (618) bolus dosage has been initiated, or after the user has declined the suggested (612) and modified dosages (618), the controller device 200 automatically returns to the closed-loop delivery mode (see FIG. 5) at operation 620.

Figure 6B:
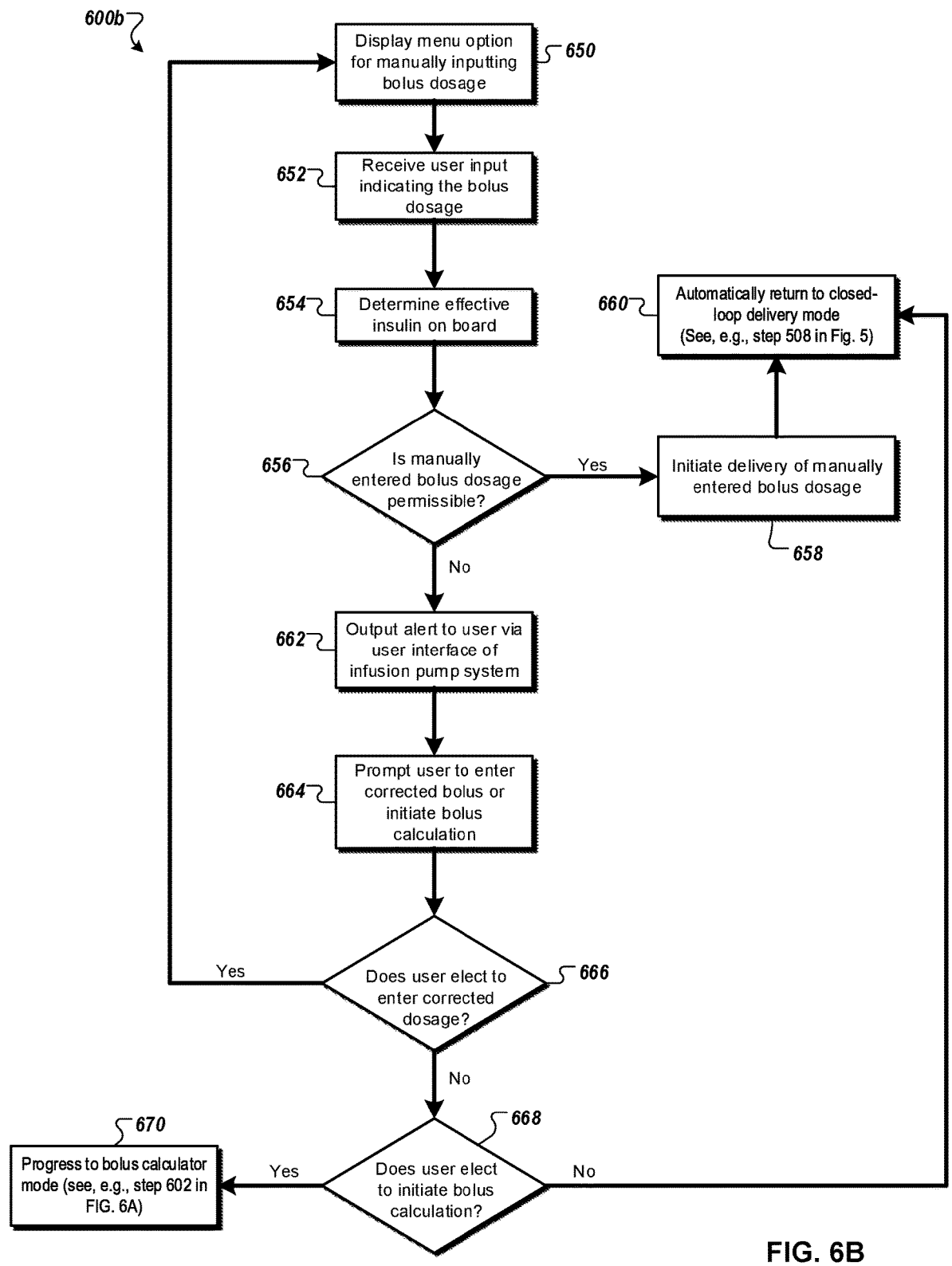
FIG. 6B is a flowchart of a second example process for temporarily interrupting a closed-loop delivery mode for providing a manually-initiated bolus dosage, in accordance with some embodiments.

FIG. 6B depicts a second example process 600b for interrupting the closed-loop delivery mode to provide a manually-initiated bolus dosage, for example, where medicine dosages (e.g., bolus dosages of insulin) are entered manually by the user. As described above with reference to FIGS. 4A-4C, the controller device 200 may determine whether the manually entered bolus dosage is likely to stack with previous dosages implemented during closed-loop operations of the infusion pump system 1 to cause systems of hypoglycemia. If adverse symptoms are likely, the controller device 200 can alert the user and prevent delivery of the requested dosage.

Referring in more detail to FIG. 6B, in operation 650, the controller device 200 causes a menu option for manually inputting a bolus dosage to be displayed to the user via the display device 222 (see FIG. 4A). In operation 652, the controller device 200 receives user input indicating a bolus dosage requested by the user. In operation 654, the controller device 200 determines the eIOB. In operation 656, the controller device 200 determines whether the requested bolus dosage is permissible based on the eIOB in an attempt to prevent an overdose by stacking with previous dosages. In some embodiments, the controller 200 determines whether the requested bolus dosage is permissible by calculating a likely future blood glucose level resulting from the dosage, and comparing the future blood glucose level to a predetermined minimum BG level (e.g., a BG level below which the user is likely to suffer symptoms of hypoglycemia, such as about 60 to 70 mg/dL). The future blood glucose level may be calculated using one or more suitable empirical models, predictive models (e.g., fuzzy logic matrices, classifiers, regressive predictors, neural networks and/or dynamic predictors, such as described in U.S. Pat. No. 8,548,544), and/or blood-glucose calculators based on user-specific parameters (e.g., insulin sensitivity). One non-limiting example is provided below:

Future BG Level=(eIOB+Requested Dose)*Insulin Sensitivity

In some embodiments, the controller 200 determines whether the requested bolus dosage is permissible by determining whether a stacking value, calculated as the sum of the requested bolus dosage and the eIOB (see definition describe above), is above a predetermined threshold. The stacking threshold may be determined as the amount of insulin likely to cause the user to suffer symptoms of hypoglycemia, which may optionally be reduced by some safety margin (e.g., 10%-20%). In some embodiments, the stacking threshold is determined based on the unique physiological characteristics of the user. For example, the stacking threshold may be manually entered into the controller device 200 by a healthcare professional or determined based on historical logs of insulin dosage. For instance, the stacking threshold may be determined as the highest amount of total insulin-on-board during closed-loop operations. As another non-limiting example, the stacking threshold may be calculated as:

$$\text{Stacking Threshold} = (\text{Current BG Level} - \text{Minimum BG Level})/\text{Insulin Sensitivity},$$

where Minimum BG Level represents the blood glucose level below which a user may begin to experience symptoms of hypoglycemia.

In operation 658, if the requested bolus dosage is permissible (656), the controller device 200 initiates delivery of the manually entered bolus dosage. The controller device 200 then automatically returns to the closed-loop delivery mode (see FIG. 5) at operation 660. In operations 662, if the stacking requested bolus dosage is not permissible (656), the controller device 200 outputs and alert to the via the user interface 220 of the infusion pump system 1 (see FIG. 4B). Then, in operation 664, the controller device 200 prompts the user to enter a corrected bolus or to initiate a bolus calculation (see. FIG. 4C). If the user elects to enter a corrected bolus dosage manually (666), the controller device 200 returns to operation 650, where the appropriate menu option is displayed. If the user elects to initiate a bolus calculation (668), the controller device progresses to a bolus calculator mode, such as described with reference to FIG. 6A. If the user neither elects to enter a corrected bolus manually (666) or to initiate a bolus calculation (668), the controller device 200 then automatically returns to the closed-loop delivery mode at operation 660. In some embodiments, the controller device 200 may automatically reduce the requested bolus dosage to a permissible amount without further user input.

While the processes described above are directed to a technique including an interruptible closed-loop delivery mode. In some implementations, the controller device may facilitate the dispensation of a bolus dosage "on top" of the closed-loop operations. So, for example, the controller device may continue the automatic dispensation of insulin according to a suitable artificial pancreas scheme, without interruption, as the user manually requests and initiates a bolus dosage. The above-described operations for safely facilitating the user-requested bolus dosage based on eIOB may be conducted concurrently with the closed-loop operations. The dispensed bolus dosage can be accounted for by the controller device in predicting a future blood glucose level of the user in accordance with predictive closed-loop control techniques.

In some implementations, a controller device (e.g., the controller device 200) can operate an infusion pump system (e.g., the infusion pump system) according to a closed-loop mode of control configured to account for glucagon medication (as an alternative to, or in addition to, the insulin medication). The infusion pump system may be able to dispense the glucagon directly or merely suggest to the user that a manual dosage should be injected (e.g., via a pen applicator). In some implementations, the controller device may interrupt closed-loop operations to suggest and dispense (or suggest and wait for a manual injection) a glucagon bolus in response to a determination (or a prediction, as discussed above) that the user's blood glucose level is (or is likely to be) below a certain target level. In some implementations, the controller device may suggest and dispense the glucagon bolus "on top" (e.g., without interruption) of the closed-loop operations. For example, the controller device may continue any monitoring or calculating processes in the closed-loop delivery mode, and merely cease insulin dispensation, in response to a low BG level determination.

The controller device in these implementations can determine a suggested glucagon dose for the user to achieve the target blood glucose level. The suggested glucagon dose can be displayed to the user to cause the user to confirm dispensation by the infusion pump device or manually administer glucagon to achieve a blood glucose level that is proximate to the target level (or is within the target level range). If the target blood glucose level is a range, the suggested glucagon dose can be determined to cause the user's blood glucose level to reach the bottom value of the range, to reach a mid-point value of the range, or to reach another specified value within the range (for example, a suggested glucagon dose can be calculated to cause the user's blood glucose level to at least exceed a value that is 5 mg/dL greater than the bottom of the target blood glucose range). The controller device can use various parameters associated with the user to determine the suggested glucagon dose for the user. For example, the controller device can use the user's current blood glucose level, the target blood glucose level, and the user's glucagon sensitivity value to determine a suggested glucagon dose according to the following formula:

$$\text{Suggested Glucagon Dose} = (\text{Target BG} - \text{Current BG})/\text{Glucagon Sensitivity}$$

Stepping through the above equation, if, for example, the user's current BG level is 50 mg/dL, the user's target BG level is 90 mg/dL, and the user's glucagon sensitivity is 20 mg/dL/Unit of Glucagon, then the above equation would be solved as:

$$\text{Suggested Glucagon Dose} = (90-50)/20 = 40/20 = 2\,\text{Units of Glucagon}$$

Depending upon the concentration of the glucagon fluid, a "Unit" of glucagon correlates to a particular number of milligrams (mg) or micrograms (mcg) of Glucagon. For example, in this embodiment, a "Unit" of glucagon correlates to 0.4 mg of glucagon, so the suggested glucagon dose of 2 Units of glucagon would be 0.8 mg of glucagon.

In some embodiments, rather than a current BG level for the user, a projected BG level for the user can be identified based on a determined BG level rate of change for the user and a previously identified BG level for the user. The controller device can then use the projected BG level to determine a suggested glucagon dose according to the following formula:

$$\text{Suggested Glucagon Dose} = (\text{Target BG} - \text{Projected BG})/\text{Glucagon Sensitivity}$$

As described above, additional parameters can also be used when determining a suggested glucagon dosage to achieve a target BG level for the user. For example Insulin on Board (JOB) or Total Insulin Load (TIL) values can be used in combination with an insulin sensitivity for the user when determining a suggested glucagon dose. For example, IOB can be used to determine a suggested glucagon dose for the user according to the formula:

$$\text{Suggested Glucagon Dose} = (\text{Target BG} - \text{Current BG} - (\text{IOB}/\text{insulin Sensitivity}))/\text{Glucagon Sensitivity}$$

Similarly, TIL can be used to determine a suggested glucagon dose for the user according to the formula:

$$\text{Suggested Glucagon Dose} = (\text{Target BG} - \text{Current BG} - (\text{TIL}/\text{Insulin Sensitivity}))/\text{Glucagon Sensitivity}$$

Another factor that can be considered when determining the suggested glucagon dose is a recent activity of the user. The effect of an activity on a user can be quantified as an activity level divided by an activity sensitivity for the user (where the activity sensitivity defines how the user's BG level changes in response to activity). Activity level can be used to determine a suggested glucagon dose for the user according to the formula:

Suggested Glucagon Dose=(Target BG−Current BG−(Activity Level/Activity Sensitivity))/Glucagon Sensitivity Yet another parameter that can be taken into consideration when determining the suggested glucagon dose for the user is Food on Board (FOB). For example, the FOB value can indicate a number of grams of carbohydrates ingested by the user. This value can be utilized along with a "carb ratio" for the user (i.e., a ratio indicating effect of carbohydrates on the BG level of the user). FOB can be a time sensitive function where food action is assumed to decay over a period of time from the time of ingestion. Food action may vary based on the content of the food, with protean and fat components having a longer time function in comparison to high glycemic index carbohydrates, which have a very short time function and low glycemic index carbohydrates, which have a moderate time function. FOB can be used to determine a suggested glucagon dose for the user according to the formula:

Suggested Glucagon Dose=(Target BG−Current BG+(FOB/Carb Ratio))/Glucagon Sensitivity Another parameter that can be taken into consideration when calculating a suggested glucagon dose is glucagon on board (GOB). The GOB value can be, for example, received from a glucagon administration device, or be entered into a suggested glucagon dose calculator manually by a user. The GOB can be, for example, a measure of the amount of glucagon in a user's system that has not yet been processed. GOB can be used to determine a suggested glucagon dose for the user according to the formula:

Suggested Glucagon Dose=(Target BG−Current BG)/Glucagon Sensitivity−GOB

It should be understood from the teachings herein that, in some embodiments, any combination of the aforementioned parameters can be taken into consideration by the glucagon dosage calculator when calculating a suggested glucagon dose. For example, in particular embodiments, all of these aforementioned parameters can be taken into account when calculating a suggested glucagon dose:

Suggested Glucagon Dose=[Target BG−Current BG−(IOB/insulin Sensitivity)−(Activity Level/Activity Sensitivity)+(FOB/Carb Ratio)]/Glucagon Sensitivity−GOB (Note that TIL can be implemented instead of IOB.)

Other combinations of the above discussed parameters can be used when determining a suggested glucagon dose for the user. Additional parameters could also be used in determining a suggested blood glucagon dose for the user.

Figure 7:
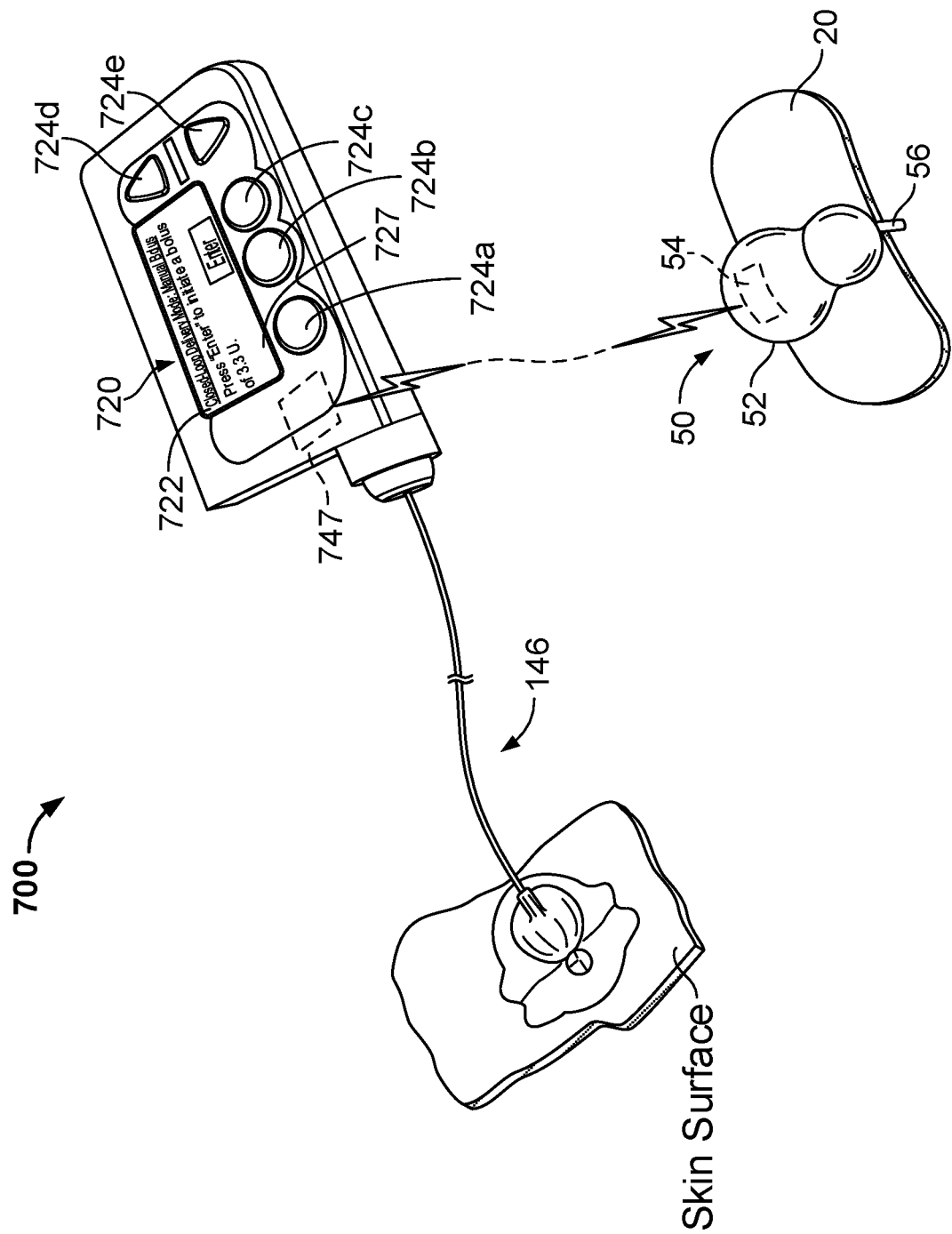
FIG. 7 is a perspective view of a second example infusion pump system, in accordance with some embodiments.

Referring now to FIG. 7, some embodiments of a portable infusion pump system 700 suitable for use in connection with one or more of the above-describes techniques (see, e.g., FIGS. 5, 6A and 6B) can employ a reusable pump apparatus (rather than a disposable pump device as previously described). In such circumstances, the infusion pump system 700 may comprise a reusable device that houses the control circuitry and the pump drive system within a single housing construct. Accordingly, the pump system 700 comprises a reusable pump device that houses both the control circuitry and the pump drive system (which may include a piston rod and one or more gears). Also, the pump system 700 can include a housing structure that defines a cavity in which a medicine cartridge can be received (not shown in FIG. 7; refer for example to cartridge 120 in FIG. 2). For example, the pump system 700 can be adapted to receive a medicine cartridge in the form of a carpule that is preloaded with insulin or another medicine. The pump drive system can act upon the fluid cartridge to controllably dispense medicine through an infusion set 146 and into the user's tissue or vasculature. In this embodiment, the user can wear the portable pump system 700 on the user's skin under clothing or in the user's pocket while receiving the medicine dispensed through the infusion set 146.

The pump system 700 can also communicate with the aforementioned glucose monitoring device 50 for the purpose of receiving data indicative of a user's blood glucose level. As shown in FIG. 7, the glucose monitoring device 50 can include the housing 52, the wireless communication device 54, and the sensor shaft 56 (similar to the embodiment described in connection with FIG. 1). In response to the measurements made by the sensor shaft 56, the glucose monitoring device 50 can employ the wireless communication device 54 to transmit data to a corresponding wireless communication device 747 housed in the pump system 700.

As previously described in connection with FIGS. 5, 6A and 6B, the control circuitry housed in the pump system 700 may be configured to facilitate the delivery of insulin dosages according to an interruptible closed-loop delivery mode of operations. That is, the closed-loop delivery mode may be temporarily interrupted to accommodate a user-prompted bolus dosage. For example, the user may elect to manually enter a requested bolus dosage or to initiate a bolus dosage calculation by the pump system 700 via the user interface 720 (e.g., the display device 722 and the user-interface buttons 724a-d). The amount of eIOB, which corresponds to the net amount of remaining active insulin in the user's system over a selected time period, influences the any manually-initiated bolus dosage (which may be calculated by the pump system 700). For example, the pump system 700 may determine that a manually entered bolus dosage is likely to stack with the eIOB to cause the user to experience adverse symptoms. In this scenario, the pump system 700 may provide an alert to the user, prevent dispensation of the requested dosage, and prompt the user to pursue a corrected dosage. Similarly, the pump system 700 may account for the eIOB in any dosage calculations prompted by the user.

A number of embodiments of the invention have been described. Nevertheless, it will be understood that various modifications may be made without departing from the spirit and scope of the invention. Accordingly, other embodiments are within the scope of the following claims.

What is claimed is:

1. A method of operating a portable insulin infusion pump system, comprising:
   while operating an infusion pump system to automatically dispense insulin according to a closed-loop delivery mode, detecting a trigger event from a user to initiate a user-selected manual bolus dosage;
   temporarily interrupting the closed-loop delivery mode;
   receiving a user input for the user-selected manual bolus dosage;
   calculating, by the infusion pump system, a calculated dosage amount of the user-selected manual bolus dosage based upon both the user input and an amount of insulin dispensed during the closed-loop delivery mode over a time period immediately prior to said interrupting;

dispensing from the infusion pump system the calculated dosage amount;

determining that the user-selected manual bolus dosage is administered; and automatically returning to the closed-loop delivery mode in response to determining that the user-selected manual bolus dosage is administered.

2. The method of claim 1, wherein the closed-loop delivery mode causes the infusion pump system to dispense insulin in response to feedback information of a user's blood glucose level, and wherein the trigger event comprises actuation of a user interface button indicating a user's request to manually initiate a bolus dispensation that is independent from said feedback information of the user's blood glucose characteristic.

3. The method of claim 1, wherein the trigger event comprises actuation of a user interface button indicating a user's request to initiate calculation of a suggested bolus dosage by the infusion pump system.

4. The method of claim 1, wherein the infusion pump system comprises a controller including: a user interface display device, control circuitry arranged in a controller housing and being programmed to perform said calculation of the calculated dosage amount of the user-selected manual bolus dosage.

5. The method of claim 4, wherein the infusion pump system comprises a pump device including: a pump housing that houses a drive system and an insulin reservoir, the controller housing being removably mountable to the pump housing so that the controller is electrically connected to the drive system.

6. The method of claim 1, wherein said amount of insulin dispensed during the closed-loop delivery mode over the time period comprises an effective-insulin-on-board amount calculated as follows:

Effective Insulin-on-Board=[Σ(Dosage$_n$*Duration Factor(t)$_n$)]−Estimated Basal Rate, where n is any positive whole number, and where Duration Factor(t)$_n$, represents a factor discounting the dosage based on an amount of time (t) since its delivery.

7. The method of claim 6, further comprising outputting an alert from the infusion pump system in response to a calculated stacking value exceeding a predetermined stacking threshold, wherein the calculated stacking value comprises the calculated dosage amount of the user-selected manual bolus dosage plus the Effective Insulin-on-board.

8. The method of claim 6, wherein the calculated dosage amount of the user-selected manual bolus dosage comprises a calculation of a suggested bolus dosage according to the following function:

Suggested Bolus Dosage=(Food Offsetting Component)+(Blood Glucose Correction Component)−(Effective Insulin-on-board Component).

9. The method of claim 6, wherein the Estimated Basal Rate is calculated according to the following function:

Estimated Basal Rate=Total Dose/(T*Scale Down Factor), where T is a unit of time.

10. A medical infusion pump system, comprising:
a portable pump housing configured to receive medicine for dispensation to a user, the pump housing at least partially containing a pump drive system to dispense the medicine through a flow path to the user; and a controller that controls the pump drive system to:
dispense the medicine from the portable pump housing according to a closed-loop delivery mode in which the controller autonomously provides insulin dosages to the user in response to feedback information of a user's blood glucose level;

receive user input to initiate a user-prompted bolus dosage;

in response to receiving the user input to initiate the user-prompted bolus dosage, temporarily interrupt the closed-loop delivery mode;

receive a user input for the user-prompted bolus dosage;

calculate, by the infusion pump system, a calculated dosage amount of the user-prompted bolus dosage based upon both the user input for the user-prompted bolus dosage and an amount of insulin dispensed during the closed-loop delivery mode over a time period immediately prior to said interrupting;

dispense from the infusion pump system the user-prompted bolus dosage;

determine that the user-selected manual bolus dosage is administered; and automatically return to the closed-loop delivery mode in response to determining that the user-selected manual bolus dosage is administered.

11. The system of claim 10, wherein the input to initiate the user-prompted bolus dosage comprises actuation of a user interface button indicating a user request to manually enter a bolus dosage amount.

12. The system of claim 10, wherein the input to initiate the user-prompted bolus dosage comprises actuation of a user interface button indicating a user request to initiate a calculation, by the infusion pump system, of a suggested bolus dosage.

13. The system of claim 10, wherein the controller comprises a user interface including a display device and a plurality of buttons.

14. The system of claim 13, wherein the controller comprises a controller housing that removably attaches to the pump housing.

15. The system of claim 14, wherein the controller is electrically connected to the pump drive system when the controller housing is removably attached to the pump housing.

16. The system of claim 15, wherein the controller is a reusable device and the pump housing and pump drive system are disposable and nonreusable.

17. The system of claim 10, further comprising a monitoring device that communicates glucose information to the controller, the glucose information being indicative of a blood glucose level of the user.

18. A portable infusion pump system, comprising:
a portable pump housing configured to receive medicine for dispensation to a user, the pump housing at least partially containing a pump drive system to dispense the medicine through a flow path to the user;

control circuitry that controls the pump drive system to dispense the medicine from the portable pump housing according to a closed-loop delivery mode in which insulin is dispensed in response to feedback information of a user's blood glucose characteristic; and a user interface in communication with the control circuitry and being configured to receive user input to interrupt said closed-loop delivery mode, wherein the control circuitry is configured to:
- temporarily interrupt the closed-loop delivery mode in response to the user input to interrupt said closed-loop delivery mode;
- receive manual bolus dosage information indicative of user input received by the user interface, the manual bolus dosage information indicating a numeric value associated with a manual bolus dosage;
- calculate a calculated dosage amount for the manual bolus dosage based upon the manual bolus dosage information;
- dispense from the infusion pump system the manual bolus dosage;
- determine that the manual bolus dosage is administered; and
- restart the closed-loop delivery mode in response to determining that the manual bolus dosage is administered.

\* \* \* \* \*

UNITED STATES PATENT AND TRADEMARK OFFICE
CERTIFICATE OF CORRECTION

PATENT NO. : 10,603,433 B2  
APPLICATION NO. : 15/848622  
DATED : March 31, 2020  
INVENTOR(S) : Mark C. Estes Page 1 of 1

It is certified that error appears in the above-identified patent and that said Letters Patent is hereby corrected as shown below:

On the Title Page
In ITEM (71) change "Milipitas, CA (US)" to --Milpitas, CA (US)--

Signed and Sealed this
Sixteenth Day of June, 2020

Andrei Iancu
*Director of the United States Patent and Trademark Office*